US009718860B2

(12) United States Patent
Cho et al.

(10) Patent No.: US 9,718,860 B2
(45) Date of Patent: Aug. 1, 2017

(54) COMPLEX OF A PROTEIN COMPRISING ZINC OXIDE-BINDING PEPTIDES AND ZINC OXIDE NANOPARTICLES, AND USE THEREOF

(75) Inventors: Nam-Hyuk Cho, Seoul (KR); Taek-Chin Cheong, Gyeonggi-do (KR); Seung-Yong Seong, Seoul (KR); Ji Hyun Min, Seoul (KR); Jun Hua Wu, Seoul (KR); Young-Keun Kim, Seoul (KR)

(73) Assignees: KOREA UNIVERSITY RESEARCH AND BUSINESS FOUNDATION (KR); SNU R&DB FOUNDATION (KR)

( * ) Notice: Subject to any disclaimer, the term of this patent is extended or adjusted under 35 U.S.C. 154(b) by 283 days.

(21) Appl. No.: 13/505,705

(22) PCT Filed: Nov. 3, 2010

(86) PCT No.: PCT/KR2010/007726
§ 371 (c)(1),
(2), (4) Date: May 2, 2012

(87) PCT Pub. No.: WO2011/055980
PCT Pub. Date: May 12, 2011

(65) Prior Publication Data
US 2012/0219504 A1    Aug. 30, 2012

(30) Foreign Application Priority Data

Nov. 3, 2009   (KR) .................. 10-2009-0105510

(51) Int. Cl.
| A61K 39/00 | (2006.01) |
| A61K 38/00 | (2006.01) |
| C07K 7/06 | (2006.01) |
| C07K 7/08 | (2006.01) |
| C07K 14/01 | (2006.01) |
| C07K 14/00 | (2006.01) |

(52) U.S. Cl.
CPC ............ *C07K 7/08* (2013.01); *A61K 39/0011* (2013.01); *C07K 7/06* (2013.01); *C07K 14/001* (2013.01); *A61K 38/00* (2013.01); *A61K 2039/55555* (2013.01)

(58) Field of Classification Search
None
See application file for complete search history.

(56) References Cited

U.S. PATENT DOCUMENTS

| 6,998,137 B2 * | 2/2006 | Shih et al. ................. 424/426 |
| 2006/0035223 A1 * | 2/2006 | Naik et al. ..................... 435/6 |
| 2010/0173360 A1 * | 7/2010 | Umetsu .................. C07K 16/44 435/69.6 |

FOREIGN PATENT DOCUMENTS

| EP | 2128249 A1 | 12/2009 |
| JP | WO 2008099968 A1 * | 8/2008 |

OTHER PUBLICATIONS

Wan, J., et al., "Synthesis and characterization of Fe3O4@ZnO core-shell structured nanoparticles", 2009, Materials Chemistry and Physics, pp. 30-32.*
Hong, R.Y., et al., "Preparation, characterization and application of Fe3O4/ZnO core/shell magnetic nanoparticles", 2008, Materials Research Bulletin, pp. 2457-2468.*
Hanley, C., et al., "The Influences of Cell Type and ZnO Nanoparticle Size on Immune Cell Cytotoxicity and Cytokine Induction", 2009, Nanoscale Res. Lett., pp. 1409-1420.*
Hsu, F.J., et al., "Vaccination of patients with B-cell lymphoma using autologous antigen-pulsed dendritic cells", 1996, Nature Medicine, pp. 52-58.*
Langerman, S., et al., "Prevention of Mucosal *Escherichia coli* Infection by FimH-Adhesin-Based Systemic Vaccination", 1997, Science, pp. 607-611.*
Kant, K.M., "Investigation of electrical transport and magnetic properties of magnetite and carbon based nanostructures", Madras Dept. Physics, 2008, pp. 1-16.*
Wilhelmi, V., et al., "Zinc Oxide Nanoparticles Induce Necrosis and Apoptosis in Macrophages in a p47phox- and Nrf2-Independent Manner", PLOS One, 2013, pp. 1-15.*
Cho et al. (2011) Nature Nanotechnology 6:675-702 "A multifunctional core-shell nanoparticle for dendritic cell-based cancer immunotherapy".
International Search Report mailed Jul. 21, 2011 for International Patent Application No. PCT/KR2010/007726.
Thai et al., "Identification and Characterization of Cu$_2$O- and ZnO-Binding Polypeptides by *Escherichia coli* Cell Surface Display: Toward an Understanding of Metal Oxide Binding", Biotechnolgy and Bioengineering, vol. 87, No. 2, pp. 129-137, Jun. 16, 2004.
Kjaergaard et al., "Sequestration of Zinc Oxide by Fimbrial Designer Chelators", Applied Environmental Microbiology, vol. 66, No. 1, pp. 10-14, Jan. 31, 2000.
Umetsu et al., "Bioassisted Room-Temperature Immobilization and Mineralization of Zinc Oxide—The Structural Odering of ZnO Nanoparticles into a Flower Type Morphology", Advanced Materials, vol. 17, pp. 2571-2575, Sep. 22, 2005.
Tomczak et al., "Morphological control and assembly of zinc oxide using a biotemplate", Acta Biomaterialia, vol. 5, pp. 876-882, Dec. 6, 2008.

(Continued)

*Primary Examiner* — Michael G Hartley
*Assistant Examiner* — Lance Rider
(74) *Attorney, Agent, or Firm* — Swanson & Bratschun, L.L.C.

(57) ABSTRACT

The present invention relates to a complex of a protein comprising zinc oxide-binding peptides and zinc oxide nanoparticles, to the use thereof as a drug delivery carrier for manufacturing medicines, and to a vaccine composition and a contrast agent comprising the composite. The protein comprising zinc oxide-binding peptides significantly improves the in vivo availability of zinc oxide-binding peptides, and therefore the complex of the present invention can be used not only as a drug delivery carrier for in vivo drug delivery or intracellular drug delivery, but also for in vivo imaging or cell imaging. The complex can be used for producing separating agents for effectively separating biological materials, therapeutic agents for hyperthermia, etc., contrast agents for MRI, and beads applicable to biosensors.

6 Claims, 14 Drawing Sheets

(56) References Cited

OTHER PUBLICATIONS

Sugita et al. (2007) Department of Biotechnology, School of Engineering, Nagoya University "Analysis of Peptide Sequence bonded to Zinc Oxide Particles using Peptide Array".

De Freitas e Silva et al. "Dendritic cell-based approaches in the fight against diseases", Frontiers in Immunology, (2014) vol. 5(78): 1-4.

Tameler et al. "Molecular biomimetics: Utilizing nature's molecular ways in practical engineering", Acta Biomaterialia 3 (2007) 289-299.

EP Office Action for Application No. 10828515.6, dated Feb. 12, 2016, 4 pages.

* cited by examiner

COMPLEX OF A PROTEIN COMPRISING ZINC OXIDE-BINDING PEPTIDES AND ZINC OXIDE NANOPARTICLES, AND USE THEREOF

RELATED APPLICATIONS

This application is a 35 U.S.C. §371 national phase application of PCT/KR2010/007726 (WO 2011/055980), filed on Nov. 3, 2010, entitled "Composite of a Protein Comprising Zinc Oxide-Bonding Peptides and Zinc Oxide Nanoparticles, and Use Thereof", which application claims the benefit of Korean Patent Application No. 10-2009-0105510, filed Nov. 3, 2009, which is incorporated herein by reference in its entirety.

TECHNICAL FIELD

The present invention relates to a complex of a protein comprising zinc oxide-binding peptides and zinc oxide nanoparticles, the use thereof as a drug delivery carrier for manufacturing a medicine, a vaccine composition comprising the composite, and a contrast agent comprising the composite.

Incorporated by reference herein in its entirety is the Sequence Listing, entitled "PCT.KR2010.007726_Sequence Listing_ST25.txt," which was created Apr. 27, 2012, size 1.36 kilobyte.

BACKGROUND ART

Nano technology has been applied in various fields. Especially, it has been most widely used in the fields of medicine and biotechnology. In the field of medicine, nano technology is applied to the fast and effective base sequence analysis enabling a revolution in treatment and diagnosis or to the nano sensing analysis that can prevent and diagnose human diseases. Also, in the field of biotechnology, it is used for the delivery of a gene or a drug, or the analysis technique based on a nano array.

Recently, various materials have been used to manufacture nanoparticles with various sizes. Nanoparticles are used for immune therapy, magnetic resonance imaging (MRI) diagnosis, drug delivery system development, and the like.

Among these, zinc oxide nanoparticles are widely used in the fields of ceramics, electric materials, sensors, and medicine and biology because of their electrical and optical properties. In particular, they have recently been widely used to develop biological detection apparatuses and the like through nanostructure synthesis using zinc oxide and organic material. In addition, they have low human health hazards (materials that have been approved by the US Food and Drug Administration as food additives) and thus are widely used as ointments, pigments, food additives, and the like in the industrial fields of medicine and medical supplies, and food. Therefore, the zinc oxide nanoparticles are being recognized as a material with very high biocompatibility, and are expected to be used in various biomedical science fields in the future.

A process of binding with biopolymers, such as a protein, is necessary in order to utilize the zinc oxide nanoparticles in the biomedical science fields. However, in most cases, the process of chemically treating the surfaces of the zinc oxide nanoparticles is introduced because the above-mentioned materials themselves do not bond strongly with other organic materials.

However, in the process of treating the surfaces of the zinc oxide nanoparticles, an organic solvent or a compound with high chemical reactivity should be used, which is limiting on the preparation of nanoparticles or structures that can be directly used for the human body and the applications thereof.

DISCLOSURE

Technical Problem

The present invention relates to the zinc oxide nanoparticles whose biocompatibility is modified using the zinc oxide-binding peptides, and which are used as a drug delivery carrier for manufacturing a medicine, or which are used in the preparation of a vaccine, a contrast agent, a separating agent that can effectively separate a biological material, a therapeutic agent for hyperthermia etc., thermotherapy, beads which are applicable for a biosensor, and the like.

Technical Solution

The inventors have found that bioavailability of the zinc oxide nanoparticles is improved by introducing the zinc oxide-binding peptides instead of chemically modifying the zinc oxide nanoparticles. As shown in the following Examples, when the zinc oxide-binding peptides are introduced to the zinc oxide nanoparticles, a binding strength of a tumor antigen to be delivered using the zinc oxide nanoparticles is significantly higher compared with the group in which the zinc oxide-binding peptides were not used. Therefore, the present invention provides a complex of the protein comprising the zinc oxide-binding peptides and the zinc oxide nanoparticles.

The zinc oxide-binding peptides to be used herein refer to peptides with excellent affinity to the zinc oxide nanoparticles as compared with general peptides. As shown in the following Examples, when the zinc oxide-binding peptides are not used, the protein drug hardly bonds to the zinc oxide nanoparticles. However, when the zinc oxide-binding peptides are used, a drug, such as a protein, DNA, RNA, and the like, can be introduced to the zinc oxide nanoparticles even if no specific chemical fixation method is used.

A method of finding the peptides binding to zinc oxide through a peptide library screening has been disclosed (Kjaergaard et al., 2000 App. Env. Microbiol. 66(1) 10-14; Thai et al., 2004 Biotech. Bioengineering. 87(2) 129-137). However, although these articles disclose that binding to zinc oxide is indirectly confirmed by measuring the number of E. coli expressing peptides on the surface thereof, they do not disclose a detailed analysis about the binding strength. Moreover, the articles do not disclose that a complex formed by introducing the zinc oxide-binding peptides to the zinc oxide nanoparticles can be used as a drug delivery carrier, a vaccine, or a contrast agent, and the like.

It is found that the zinc oxide-binding peptides preferably have the configuration of the following Formula I or Formula II through the result of analyzing an amino acid sequence of the zinc oxide-binding peptides using the peptide library as disclosed in the above-mentioned prior art.

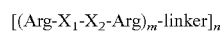  [Formula I]

$[(\text{Arg-}X_1\text{-}X_2\text{-Arg})_m\text{-linker}]_n$        [Formula I]

  [Formula II]

$[(\text{Arg-}X_1\text{-}X_2\text{-Arg-Lys})_m\text{-linker}]_n$        [Formula II]

wherein,
X$_1$ is Pro, Ala, Thr, Gln, or Ile;
X$_2$ is His, Ile, Asn, or Arg;
m is an integer of 1 to 5; and
n is an integer of 1 to 100.

That is, it is found that the binding strength of the zinc oxide-binding peptides to zinc oxide is increased by having a tandem repeat structure while commonly comprising Arg-X$_1$-X$_2$-Arg or Arg-X$_1$-X$_2$-Arg-Lys motif. A linker, to which the motifs can flexibly bond, is included in order to have the tandem repeat structure. Gly-Gly-Asp-Ala is used as the linker in the following Examples, but it is not specifically limited as long as it can provide flexibility to bonds between the motifs. For example, several Gly may be preferably included in the linker. For example, a type of Gly-Gly-Asp-Xaa-Ala (Xaa refers to any amino acid) may also be used as the linker. Ser or Val is expected to be preferable as Xaa. As confirmed in the following Examples, the zinc oxide-binding peptides have very excellent binding strength to zinc oxide and thus may be used for surface-modification of the zinc oxide nanoparticles to use the zinc oxide nanoparticles in vivo or in a cell.

Therefore, the present invention provides the complex of the zinc oxide nanoparticles and the protein comprising the zinc oxide-binding peptides of the following Formula I or Formula II.

  [Formula I]

  [Formula II]

wherein,
X$_1$ is Pro, Ala, Thr, Gln, or Ile;
X$_2$ is His, Ile, Asn, or Arg;
m is an integer of 1 to 5; and
n is an integer of 1 to 100.

In one embodiment, X$_1$ is Pro or Thr, X$_2$ is His, m is an integer of 1 to 5, and n is an integer of 3 to 50.

In another embodiment, the zinc oxide-binding peptides may be peptides having any one amino acid sequence of SEQ ID NO: 1 to SEQ ID NO: 4.

SEQ ID NO: 1:
Arg Pro His Arg Lys Gly Gly Asp Ala

SEQ ID NO: 2:
Arg Thr His Arg Lys Gly Gly Asp Ala

SEQ ID NO: 3:
Arg Pro His Arg Lys Gly Gly Asp Ala Arg Pro His Arg

Lys Gly Gly Asp Ala Arg Pro His Arg Lys Gly Gly Asp

Ala

SEQ ID NO: 4:
Arg Thr His Arg Lys Gly Gly Asp Ala Arg Thr His Arg

Lys Gly Gly Asp Ala Arg Thr His Arg Lys Gly Gly Asp

Ala

For the present invention, the protein comprising the zinc oxide-binding peptides may be the zinc oxide-binding peptides of Formula I or Formula II itself. In this situation, the complex of the protein comprising the zinc oxide-binding peptides and the zinc oxide nanoparticles may further introduce a protein, DNA, RNA, or a drug, such as a compound medicine, a contrast medium, and the like. For example, the drug may be chemically or physically bonded to the composite, which functions to deliver the drugs in vivo or in a cell.

In this case, a target-directed ligand may bond to the surface of the complex for effective delivery of the drug. This refers to a ligand for targeting to introduce the complex of the present invention to a tissue or cell. As the target-directed ligand, a compound ligand that is known to bond to a specific receptor of the cell surface, as well as an antibody and aptamer, may also be usefully used. The specific type of the above-mentioned antibody, aptamer, and compound ligand is well known in the art.

The chemical or physical bond between the complex and the drug or the chemical or physical bond between the complex and the target-directed ligand may be effected through binding of drug or target-directed ligand with the protein present on the surface of the composite, and this may be easily effected through the use of methods that are known in the art.

For example, it may be accomplished through a covalent bond between the functional groups present of the protein on the surface of the complex and the functional groups present on the drug or the target-directed ligand. The functional groups may be endogenously present on the protein, drug or target-directed ligand, or the protein, drug or target-directed ligand may be modified to have the inter-combinable functional groups if necessary. The functional groups present on the protein and the functional groups present on the drug or target-directed ligand may be selected from known bonding examples of the functional groups so that they may bond to each other. Representative examples of the known bonding examples of the functional groups are shown in the following Table 1.

TABLE 1

| I | II | III |
|---|---|---|
| R—NH$_2$ | R$^+$—COOH | R—NHCO—R' |
| R—SH | R'—SH | R—SS—R |
| R—OH | R'-(Epoxy group) | R—OCH$_2$C(OH)CH$_2$—R' |
| RH—NH$_2$ | R'-(Epoxy group) | R—NHCH$_2$C(OH)CH$_2$—R' |
| R—SH | R'-(Epoxy group) | R—SCH$_2$C(OH)CH$_2$—R' |
| R—NH$_2$ | R'—COH | R—N=CH—R' |
| R—NH$_2$ | R'—NCO | R—NHCONH—R' |
| R—NH$_2$ | R'—NCS | R—NHCSNH—R' |
| R—SH | R'—COCH$_2$ | R'—COCH$_2$S—R |
| R—SH | R'—O(C=O)X | R'—OCH$_2$(C=O)O—R' |
| R-(Aziridine group) | R'—SH | R—CH$_2$CH(NH$_2$CH$_2$S—R' |
| R—CH=CH$_2$ | R'—SH | R—CH$_2$CHS—R' |
| R—OH | R'—NCO | R'—NCOO—R |
| R—SH | R'—COCH$_2$X | R—SCH$_2$CO—R' |
| R—NH$_2$ | R'—CON$_3$ | R'—NHCO—R' |
| R—COOH | R'—COOH | R—(C=O)O(C=O)—R' + H$_2$O |
| R—SH | R'—X | R—S—R' |
| R—NH$_2$ | R'CH$_2$C(NH$^{2+}$)OCH$_3$ | R'—NHC(NH$^{2+}$)CH$_2$—R' |
| R—OP(O$^{2-}$)OH | R—NH$_2$ | R—OP(O$^{2-}$)—NH—R' |
| R—CONHNH$_2$ | R'—COH | R—CONHN=CH—R' |
| R—NH$_2$ | R'—SH | R—NHCO(CH$_2$)$_2$SS—R' |

I or II: Functional groups present on a protein or functional groups present on a drug or ligand
III: Bonding examples according to the reaction of I and II.
R or R': Any functional groups In other words, the protein comprising the zinc oxide-binding peptides may be a fusion protein comprising not only the zinc oxide-binding peptides but also a second peptide fused with a protein. The fusion protein may be easily prepared through a conventional method of preparing a recombinant protein known in the art. At this time, the second peptide may be positioned at the N-terminus or the C-terminus of the zinc oxide-binding peptides, and the location is not especially limited.

For example, the second peptide included in the protein comprising the zinc oxide-binding peptides may be an antigen.

That is, in one embodiment, the protein may be a recombinant protein comprising the zinc oxide-binding peptides and an antigen.

The complex of the recombinant protein comprising the zinc oxide-binding peptides and the antigen and the zinc oxide nanoparticles may be used in various applications as will be mentioned below. For example, the complex of the recombinant protein comprising the zinc oxide-binding peptides and the antigen and the zinc oxide nanoparticles may be used to prepare a vaccine composition for immunotherapy. The zinc oxide nanoparticles may be used as a carrier or a drug delivery carrier for the delivery to the recombinant protein comprising an antigen.

In one embodiment, the antigen may be a tumor antigen. The following Examples show that the complex of the recombinant protein comprising the zinc oxide-binding peptides and the tumor antigen and the zinc oxide nanoparticles can be introduced into the dendritic cells, and then the dendritic cells can be used as a vaccine to treat or prevent cancer.

The type of the tumor antigen is not especially limited, and any tumor antigen known in the art can be used. The representative examples of the tumor antigen that can be used to treat or prevent cancer includes a carcinoma embryonic antigen, survivin, MAGE-1, MAGE-2, MAGE-3, MAGE-12, BAGE, GAGE, NY-ESO-1, tyrosinase, TRP-1, TRP-2, gp100, MART-1, MC1R, Ig idiotype, CDK4, caspase-9, beta-catenin, CIA, BCR/ABL, mutated p21/ras, mutated p53, proteinase 3, WT1, MUC-1, normal p53, Her2/neu, PAP, PSA, PSMA, G250, HPV E6/E7, EBV LMP2a, HCV, HHV-8, alpha-fetoprotein, 5T4, onco-trophoblast, glycoprotein, and the like. Examples of the tumor antigen and the cancer cell expressing them are well known in the art.

Meanwhile, the zinc oxide nanoparticles used herein are defined to include zinc oxide nanoparticles which are completely composed of zinc oxide, and also zinc oxide nanoparticles comprising other components.

In one embodiment, the zinc oxide nanoparticles of the present invention may be composed of only zinc oxide. In this case, the complex of the present invention plays a role in delivering a drug, such as protein, in vivo or in a cell through the zinc oxide nanoparticles, and it may also be optically imaged due to a natural property of the zinc oxide nanoparticles.

In one embodiment, the zinc oxide nanoparticles of the present invention may be a material with a nano size, in which the outside of the nano structure is surrounded by the zinc oxide in whole or in part. Examples of the material include a dumbbell shape, a nanowire, an alloy, a thin film, and the like. In the dumbbell shape, one side of a dumbbell may be partially or completely composed of zinc oxide, and the other side may be composed of a magnet, a metal, a polymer, a ceramic, a semiconductor, and the like. In addition, the alloy may be an alloy of zinc oxide and a metal, a ceramic or a semiconductor (for example, FeO and ZnO, or Au and ZnO). In addition, the nanowire may be prepared using an electrochemical method or a wet method. The nanowire may be a ZnO nanowire, a nanowire comprising ZnO (for example, an Au ZnO alloy nanowire), or a nanowire coated with ZnO. Moreover, the zinc oxide nanoparticles of the present invention may be a thin film with ZnO present on its surface, and also have a structure which is complexly configured according to its application (for example, a structure in which a one-dimensional nanowire protrudes from a thin film, a structure in which a particle surface adheres to a nano particle, a nanowire, and the like).

In another embodiment, the zinc oxide nanoparticles may have a core-shell structure. For the zinc oxide nanoparticles having the core-shell structure, the shell is composed of zinc oxide to bond with the protein of the present invention, and a proper material may be selected and positioned at the core for the purpose of application of the complex according to the present invention.

In one embodiment, for example, the core may be composed of a metal material, a magnetic material, a magnetic alloy, or a semiconductor material. The metal may be selected from the group consisting of Pt, Pd, Ag, Cu, and Au, but the present invention is not especially limited thereto. The magnetic material may be preferably selected from the group consisting of Co, Mn, Fe, Ni, Gd, Mo, MM'2O4, and MxOy (M and M' are each independently Co, Fe, Ni, Mn, Zn, Gd, or Cr, and $0<x\leq3$, $0<y\leq5$), but the present invention is not especially limited thereto. In addition, the magnetic alloy may be preferably selected from the group consisting of CoCu, CoPt, FePt, CoSm, NiFe, and NiFeCo, but the present invention is not especially limited thereto. In addition, the semiconductor material may be selected from the group consisting of CdSe, CdTe, ZnSe, and the like, but the present invention is not especially limited thereto.

In one embodiment, the core may be composed of the magnetic material. In this case, effective separation of a biological material (DNA, RNA, cells, and the like) by an outside magnetic field, drug delivery, high efficiency diagnosis, treatment such as hyperthermia by an outside magnetic field, MRI imaging, and the like, can be enabled using the complex of the present invention due to a magnetic material inside the zinc oxide nanoparticles.

In one embodiment, the core may be composed of a T1 or T2 contrast medium. In this case, the complex of the present invention may not only deliver the protein in vivo or in a cell through the zinc oxide nanoparticles, but it may also enable MRI contrast with the T1 or T2 contrast medium in the zinc oxide, and have a multimodal property that can enable optical imaging due to the natural property of the zinc oxide nanoparticles. The type of the T1 or T2 contrast medium that can be used for the zinc oxide nanoparticles having a core-shell structure is not particularly limited, and the examples of the T1 or T2 are well known in the art (for example, see Korean Patent Application Publication No. 10-2010-0023778).

In one embodiment, the core may be composed of an iron oxide. The following Examples show that the zinc oxide nanoparticles having a core-shell structure, in which the core is composed of an iron oxide that is a T2 contrast medium and the shell is composed of zinc oxide, were prepared, and a tumor cell was contrasted using the complex of the protein, comprising a tumor antigen and the zinc oxide-binding a peptides, and the zinc oxide nanoparticles, thus inducing apoptosis of tumor cells.

The zinc oxide nanoparticles according to the present invention may be preferably prepared using a polymer surfactant. When an amphiphilic polymer surfactant is used as the polymer surfactant, the zinc oxide nanoparticles can be prepared in an organic solvent phase using thermodecomposition, and thus zinc oxide nanoparticles with excellent crystallinity and a homogeneous size can be obtained as compared with the nanoparticles prepared using other methods, such as co-precipitation. Dispersibility in water is also relatively excellent as compared with the nanoparticles prepared in the organic solvent phase without using the amphiphilic surfactant. The amphiphilic surfactant may include poly(ethylene glycol)-block-poly (polypropylene glycol)-block-poly(ethylene glycol) (PEG-PPG-PEG) or polyvinylpyrrolidone (PVP).

Meanwhile, no specific method is required for the formation of the complex of the protein comprising the zinc oxide-binding peptides and the zinc oxide nanoparticles. The complex can be simply formed by incubation of the protein and the zinc oxide nanoparticles due to the affinity of the zinc oxide-binding peptides to the zinc oxide.

The present invention also provides a pharmaceutical composition comprising the complex of the zinc oxide nanoparticles and the protein comprising the zinc oxide-binding peptides as a drug delivery carrier. As disclosed above, the complex of the present invention can function as a drug delivery carrier that binds with a drug, such as a protein, DNA, RNA, a cell, a compound medicine or a contrast medium and delivers the drug in vivo or in a cell. The drug may physically or chemically bind with the complex as mentioned above, and the complex may be further combined with a target-directed ligand in addition to the above drug to give targetability to the composite. In addition, the pharmaceutical composition of the present invention may further include an additional drug in addition to the drug bound to the composite, and various excipients that are generally used in preparation of medicine.

The present invention also provides a method of preparing a pharmaceutical composition comprising the complex and the drug, comprising binding the drug to the complex or mixing the drug with the complex of the zinc oxide nanoparticles and the protein comprising the zinc oxide-binding peptides.

Also, the present invention provides a vaccine composition comprising the complex of the zinc oxide nanoparticles and the protein comprising the zinc oxide-binding peptides and the antigen. As mentioned above, the complex of the protein comprising the zinc oxide-binding peptides and the antigen; and the zinc oxide nanoparticles may be used to prepare a vaccine composition. The zinc oxide-binding peptides cause the antigen to bond to the zinc oxide nanoparticles so that the antigen is easily introduced in vivo or in a cell using the zinc oxide nanoparticles as a drug delivery carrier. The antigen introduced in vivo or in a cell causes a cellular or humoral immune response to the antigen so that a disease medicated by the antigen can be treated or prevented through the immune system of the human body. The type of the antigen is not specifically limited and any antigen which can be used to treat or prevent a disease by artificially causing an immune response may be used to prepare the vaccine composition of the present invention. In one embodiment, the antigen may be a tumor antigen, and in this case, the vaccine composition can be used to treat or prevent cancer.

In one embodiment of the present invention, the vaccine composition may further include an immunocyte. In the present invention, immunocyte is a generic term used to describe a cell that acts on behalf of the immune system. Especially, it includes a dendritic cell, T cell, NK cell, B cell, and the like. In one embodiment, the immunocyte may be a dendritic cell, T cell, and NK cell. Meanwhile, the composition includes a buffer solution, and the like, that can stably maintain a cell in addition to the immunocyte.

Methods for immune treatment of cancer using the immunocyte are well known in the art. For example, in such a method, the dendritic cells are collected from a patient, a fusion protein of TAT protein and a tumor antigen is introduced into the dendritic cells, and then the dendritic cells that have interacted with the tumor antigen is injected into the patient to allow the dendritic cells to induce an immune response thereby killing the tumor cells. The conventional method of introducing a tumor antigen into the dendritic cells using the TAT fusion protein is complicated in procedures and also requires a long culture time, which leads to a decrease in survival rate of the dendritic cells and a decrease in effects after being introduced in vivo. However, when the complex of the protein, comprising the zinc oxide-binding peptides and the antigen, and the zinc oxide nanoparticles of the present invention is introduced into an immunocyte and the resulting immunocyte is used for a vaccine composition, a therapeutic agent (e.g., a vaccine) for treating a cell such as an immunocyte can be simply prepared in a short period of time. In addition, as shown in the following Examples, the complex of the present invention can effectively kill a tumor cell because of its very high delivery rate of the tumor antigen without influencing the survival rate of the dendritic cell, immunity, and the like. Accordingly, in one embodiment of the present invention, the vaccine composition may comprise an immunocyte introduced with the composite.

A composition, an administration route, an effective amount, and the like, of the cancer immune therapeutic agent or vaccine composition comprising an immunocyte are well known in the art.

In addition, the present invention provides a contrast agent comprising the complex of the protein comprising the zinc oxide-binding peptides and the zinc oxide nanoparticles.

The above-mentioned complex of the protein comprising the zinc oxide-binding peptides and the zinc oxide nanoparticles may function as a drug delivery carrier or a vaccine, and also the complex itself may function as an imaging agent, because the zinc oxide nanoparticles have an optical imaging property.

In one embodiment, the complex of the protein comprising the zinc oxide-binding peptides and the zinc oxide nanoparticles may bond with a target-directed ligand. In this case, the targetability of the contrast agent can be improved.

In another embodiment, the protein comprising the zinc oxide-binding peptides may include the zinc oxide-binding peptides and an antigen. As mentioned above, when the protein comprising the zinc oxide-binding peptides includes an antigen, the complex of the present invention may be introduced to a target cell expressing the antigen to induce an immune response and also the target cell can be seen due to the contrast effect of the composite. The type of the antigen is not especially limited. In one embodiment, the antigen may be a tumor antigen, and in this case, the contrast agent can make it possible to see and immunologically treat a cancer at the same time. The tumor antigen may be selected from the group consisting of a carcinoma embryonic antigen, survivin, MAGE-1, MAGE-2, MAGE-3, MAGE-12, BAGE, GAGE, NY-ESO-1, tyrosinase, TRP-1, TRP-2, gp100, MART-1, MC1R, Ig idiotype, CDK4, caspase-9, beta-catenin, CIA, BCR/ABL, mutated p21/ras, mutated p53, proteinase 3, WT1, MUC-1, normal p53, Her2/neu, PAP, PSA, PSMA, G250, HPV E6/E7, EBV LMP2a, HCV, HHV-8, alpha-fetoprotein, 5T4, onco-trophoblast, and glycoprotein, but the present invention is not limited thereto.

The composition of the zinc oxide nanoparticles included in the contrast agent is as mentioned above. In one embodiment, the zinc oxide nanoparticles may have a core-shell structure. For example, they are composed of a metal material, a magnetic material, a magnetic alloy, or a semiconductor material and the shell may be composed of zinc oxide. As mentioned above, when the zinc oxide nanoparticles have the core-shell structure, in which the core is composed of a T1 or T2 contrast medium and the shell is composed of zinc oxide, the contrast agent of the present invention makes it possible to perform an optical imaging process and also an MRI process. As shown in the following Examples, the contrast agent of the present invention comprising the complex of the zinc oxide nanoparticles composed of iron oxide core and zinc oxide shell and the protein comprising the zinc oxide-binding peptides and the carcinoma embryonic antigen can kill a cancer cell and also simultaneously trace and diagnose the injected dendritic cell. Conventional iron oxide nanoparticles for the MRI imaging should undergo complicated procedures, such as chemical surface treatment to prevent cohesion in an aqueous solution phase, use of compounds for delivering a cell (a transfection agent), for example, a liposome to introduce to a dendritic cell, and also require a long culture time, which lead to a decrease in the survival rate of the dendritic cells and a decrease in effects after being introduced in vivo. However, when the complex of the protein, comprising the zinc oxide-binding peptides and the antigen, and the zinc oxide nanoparticles of the present invention is introduced into the dendritic cells and the resulting dendritic cells are used for a vaccine composition, a therapeutic agent (e.g., a vaccine) for treating cells such as dendritic cells can be simply prepared in a short period of time and the MRI through an iron oxide component that is included in the core-shell can be enabled.

For the contrast agent of the present invention, the protein comprising the zinc oxide-binding peptides may further include an antibody in addition to the zinc oxide-binding peptides. In this case, the antibody functions to give targetability to the imaging agent, and when the antibody is a therapeutic antibody, it may further play a role as a therapeutic agent. In one embodiment, the antibody may target a tumor antigen. The type of the antibody that gives targetability to the contrast agent or exhibits a therapeutic effect by targeting a tumor antigen is well known in the art. For example, a recombinant Herceptin antibody may be prepared by manipulating the zinc oxide-binding peptides to be present on the Fc terminus of Herceptin which is well known as an antibody for treating a cancer. The recombinant antibody may bind very well to the zinc oxide nanoparticles, and then the resulting complex may function as a therapeutic agent and a contrast agent that can treat cancer and can control prognosis after tumor treatment at the same time.

In addition, for a composition of the contrast agent, the complex may physically or chemically bind with at least one drug selected from the group consisting of a protein, DNA, RNA, a medicine compound, and a contrast medium. For example, when the complex binds with a drug for treating cancer, it can be possible to diagnose and treat the cancer at the same time. When the complex further binds with additional contrast medium, it can function as a multi-functional contrast agent. For example, a fluorescent material, a radioactive isotope or a quantum dot, and the like are included as the additional contrast agent.

The contrast agent according to the present invention may include a carrier and a vehicle that are generally used in the medical field. Specifically, the carrier and vehicle may include an ion-exchange resin, alumina, aluminum stearate, lecithin, a serum protein (for example, human serum albumin), a buffering material (for example, various phosphates, glycine, sorbic acid, potassium sorbate, a partial glyceride mixture of saturated vegetable fatty acid), water, salt or electrolyte (for example, protamine sulfate, disodium hydrogen phosphate, potassium hydrogen phosphate, sodium chloride and zinc salt), a colloid silica, magnesium trisilicate, polyvinyl pyrrolidone, cellulose-based substrate, polyethylene glycol, sodium carboxymethyl cellulose, polyarylate, wax, polyethylene glycol or lanolin, and the like, but the present invention is not limited thereto. Moreover, the contrast agent according to the present invention further includes a lubricant, a wetting agent, an emulsifier, a suspending agent, a preservative, and the like in addition to the above-mentioned components.

In one embodiment, the contrast agent according to the present invention may be prepared in the form of an aqueous solution for a parenteral administration. A buffering solution, such as Hank's solution, Ringer's solution, or physically buffered saline, may be used. A substrate that can increase the viscosity of a suspension, such as sodium carboxymethyl cellulose, sorbitol, or dextran, may be added to the water-soluble injection suspension.

Another preferable embodiment of the contrast agent of the present invention may be a formulation for a sterile injection of aqueous or oily suspension. The suspension may be formulated using a technique known in the art that uses a suitable dispersing or wetting agent (for example, Tween 80), and a suspending agent. In addition, a formulation for a sterile injection may be a sterile injection solution or suspension in a nontoxic parenteral diluent or solvent (for example, a solution in 1,3-butanediol). The vehicle and solvent that may be used herein may include mannitol, water, Ringer's solution, and an isotonic sodium chloride solution. In addition, sterile non-volatile oil is generally used as a solvent or a suspending medium. For this purpose, any of the non-volatile oils having low irritability comprising a synthetic mono- or di-glyceride can be used.

The contrast agent may be administered through a route of administration that is generally used in the medicine field. Parenteral administration is preferred, and for example, the contrast agent may be administrated through a route of intravenous, intraperitoneal, intramuscular, subcutaneous or topical administration.

Meanwhile, the complex of the protein comprising the zinc oxide-binding peptides and the zinc oxide nanoparticles of the present invention may be further used to prepare a separating agent that can effectively separate a biological material, a therapeutic agent for hyperthermia etc., an MRI contrast agent, and beads which are applicable for a biosensor, in addition to the use for preparation of a drug delivery carrier, a vaccine, or a contrast agent as mentioned above. For example, the complex of the present invention is used for an optical separation method, such as FACS, due to the optical property of the zinc oxide nanoparticles to separate a biological material, such as a gene, a cell, and the like. In another embodiment, when the complex of the protein comprising the zinc oxide-binding peptides and the zinc oxide nanoparticles of the present invention has a core-shell structure, the core is composed of the magnetic material, and the shell is composed of zinc oxide, it can be applicable for magnetic separation of a material, such as MACS due to the presence of the magnetic material on the core. In addition, the present invention provides a composition for hyperthermia comprising the complex of the protein comprising the zinc oxide-binding peptides and the zinc oxide nanoparticles, a biosensor comprising the complex of the protein comprising the zinc oxide-binding peptides and the zinc oxide nanoparticles as beads, and the like.

Effect of the Invention

Since the protein comprising the zinc oxide-binding peptides significantly improves in vivo availability of the zinc oxide nanoparticles, the complex can be used as a drug delivery carrier for delivering a medicine in vivo or in a cell, and also be used for in vivo imaging or cell imaging. In addition, the complex can be further used to prepare a separating agent that can effectively separate a biological material, a therapeutic agent for hyperthermia etc., an MRI contrast agent, and beads which are applicable for a biosensor.

MODE FOR INVENTION

Advantages and characteristics of the present invention, and a method of achieving them will become clear with reference to the following Examples as mentioned below in detail. However, the present invention is not limited to the following Examples, and various types of the present invention will be implemented in various manners. The Examples are disclosed merely to provide a complete description of the present invention and to provide complete understanding of the present invention to those skilled in the art to which the present invention belongs, and the present invention is only defined by the appended claims.

EXAMPLE

Example 1

Synthesis of $Fe_3O_4$—ZnO Core-Shell Nanoparticles $Fe_3O_4$—ZnO core-shell nanoparticles (CSNP) were prepared by a modified nano-emulsion method.

In order to synthesize an $Fe_3O_4$ core, 0.5 mmol (0.1766 g) of iron (III) acetylacetonate (Fe(acac)$_3$, 99.9%, Aldrich) and 2.5 mmol (0.6468 g) of 1,2-hexadecanediol ($C_{14}H_{29}CH(OH)CH_2(OH)$, 90%, Aldrich) were dissolved in 10 ml to 20 ml of octylether ($C_8H_{17}OC_8H_{17}$, 99%, Wako) along with poly(ethylene glycol)-block-poly(polypropylene glycol)-block-poly(ethylene glycol) (PEG-PPG-PEG, Aldrich) (0.7529 g). In order to control physical and chemical properties of the nanoparticles, polyvinylpyrrolidone (PVP) may be used instead of PEG-PPG-PEG, and oleylamine (OAM, $C_9H_{18}=C_9H_{17}NH_2$, 70%), oleic acid (OA, $C_9H_{18}=C_8H_{15}COOH$, 99%), and the like can be used as a solvent.

Figure 1:
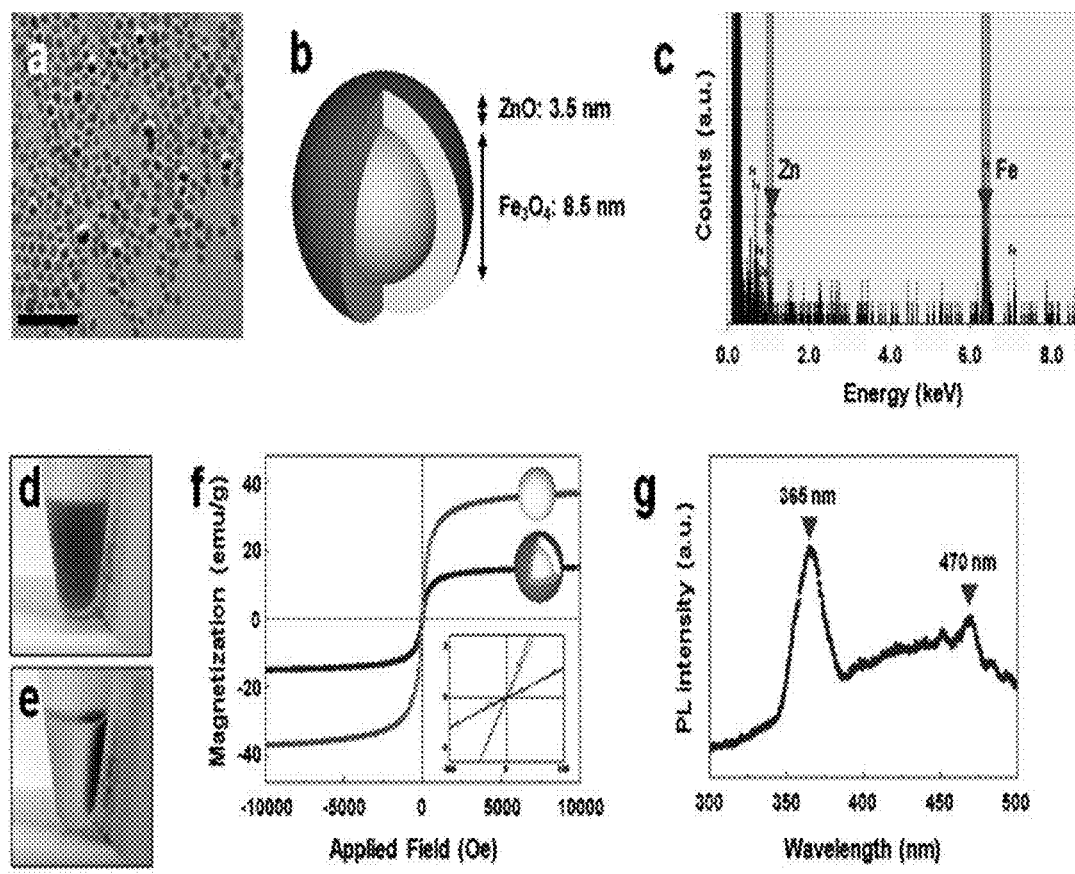
FIG. 1 shows the results of analyzing TEM analysis, a structure and component analysis, dispersibility and optical property in an aqueous solution, and a magnetic property of $Fe_3O_4$—ZnO core-shell nanoparticles.

A reduction process was performed by slowly heating the mixing solution to 80 to 130° C. for 1 hour, and then circulating for 1 to 2 hours at the above temperature. Thereafter, the mixing solution was quickly heated to 260 to 300° C. for 15 minutes, and then refluxed at 260 to 300° C. for 1 to 2 hours. The mixing solution was cooled to room temperature to form a magnetic core material. The synthesis process may be performed under an inert gas atmosphere, such as argon. After forming the magnetic core, a ZnO coating process was performed without an additional purification process. Octyl ether (5 ml) in which 0.25 mmol (0.0659 g) of zinc acetylacetonate (Zn(acac)$_2$) and 0.3234 g (1.25 mmol) of 1,2-hexdecanediol were dissolved was added to the formed $Fe_3O_4$ core. The reaction mixture was then heated to 80 to 130° C. using magnetic stirring and a heater, and then was homogenously mixed for 1 to 2 hours. Subsequently, the mixing solution was heated and maintained at 260 to 300° C. for 1 or 2 hours to form a ZnO layer on the Fe$_3$O$_4$. After the reaction, anhydrous ethanol was added to the product mixture to precipitate the Fe$_3$O$_4$—ZnO core-shell nanoparticles, which were purified and separated by centrifugation and magnetic separation. A morphology, a composition, and a nanostructure of the core-shell nanoparticles prepared were measured with a TEM (JEOL 2010F, Technai F20 (FEI Co.)) equipped with an energy dispersive X-ray spectroscopy. In order to prepare a sample for the TEM measurement, the nanoparticles dispersed in hexane and the peptide-nanoparticle complex dispersed in water and PBS were dropped on carbon-supported copper grids, respectively. A structural analysis of Fe$_3$O$_4$—ZnO NPs was performed by a powder x-ray diffraction analyzer (10C1 beamline, Pohang Accelerator Laboratory, South Korea). The magnetic property was measured by using a vibrating sample magnetometer (Lakeshore 7300) and a Physical Property Measurement System (PPMS, Quantum Design). The optical properties of the nanoparticles dispersed in hexane and the peptide-nanoparticle complex dispersed in water and PBS were analyzed by UV-Vis spectroscopy (Agilent 8453E) and spectrofluorophotometry (Shimadzu RF-5301PC), respectively. FIG. 1 shows the results of the TEM analysis, water dispersibility, a magnetic property and an optical property analysis of Fe$_3$O$_4$—ZnO nanoparticles. Specifically, FIG. 1A is the TEM result (scale bar: 100 nm) showing a globular shape and a homogeneous size distribution of Fe$_3$O$_4$—ZnO nanoparticles. FIG. 1B is a structural schematic diagram of core-shell nanoparticles. FIG. 1C is the result of TEM-EDX point-probe analysis showing that single core-shell nanoparticles are composed of Fe and Zn. FIG. 1D shows a homogeneous dispersion of brown core-shell nanoparticles in PBS, and FIG. 1E shows a clear and transparent solution after recovering the nanoparticles by a magnet. FIG. 1F shows magnetic hysteresis loops of Fe$_3$O$_4$ core part (Red) and Fe$_3$O$_4$—ZnO core-shell nanoparticles (Blue). FIG. 1G shows a photoluminescence spectrum exhibiting UV and visible light emission of the core-shell nanoparticles bonded with peptides.

Example 2

Design and Preparation of the ZnO-Binding Peptides

In order to design a ZnO-binding peptide (ZBP), sequences with high-affinity ZnO binding patterns were collected from of previous researches. It was found that a binding motif of RXXR or RXXRK plays an important role in ZnO binding through clustering of high-affinity ZnO binding peptides, and then RPHRK or RTHRK was selected as a motif of the ZnO-binding peptide to be used in the following Examples. In addition, in order to increase a binding strength between the zinc oxide nanoparticles and ZnO-binding peptides, a serial repeat of a ZnO binding motif was introduced when preparing the zinc oxide-binding peptide. GGDA was selected and then introduced between motifs as a flexible linker that can increase flexibility between neighboring motifs.

Figure 2:
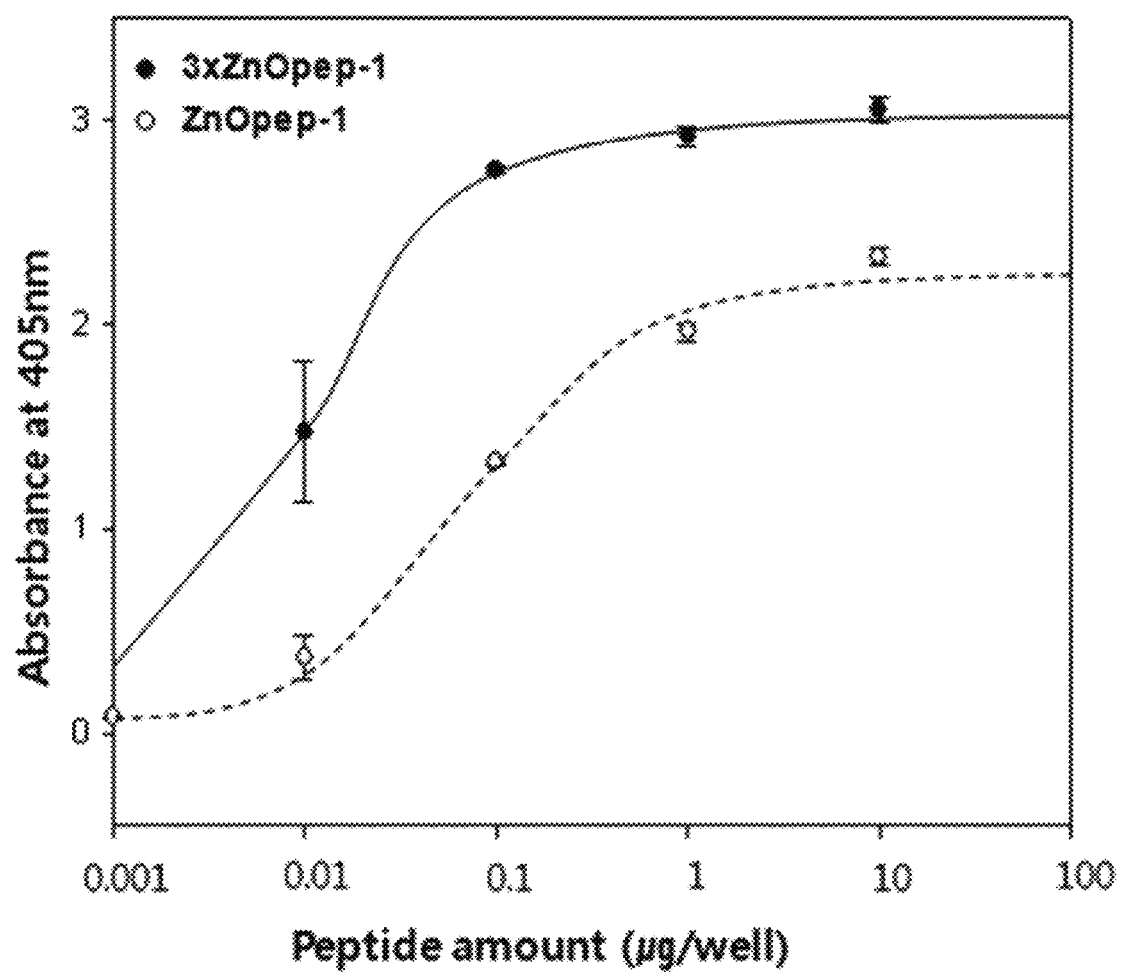
FIG. 2 shows the results of absorbance at 405 nm in which the amounts of ZnOpep-1 and 3×ZnOpep-1 of the present invention are measured.

A method of investigating the binding strength with streptavidin by labeling the zinc oxide-binding peptides with a biotin was used to quantitatively analyze the binding strength of the zinc oxide-binding peptides to the zinc oxide nanoparticles. To achieve this, a binding between the zinc oxide-binding peptides labeled with biotin and streptavidin was first confirmed. Biotin-RPHRKGGDA (biotin-ZnOpep-1), biotin-RPHRKGGDARPHRKGGDARPHRKGGDA (biotin-3×ZnOpep-1), biotin-RTHRKGGDA (biotin-ZnO-pep-2), and biotin-RTHRKGGDARTHRKGGDARTHRK-GGDA (biotin-3×ZnOpep-2) were synthesized as a peptide labeled with biotin using a peptide synthesizer (PeptrEX™, Peptron), and then dissolved in sterilized water to be 1 mg/ml. Each of the peptides diluted with tris buffered saline (TBS) was added to a 96-well plate at 10 μg/well, 1 μg/well, 0.1 μg/well, and 0.01 μg/well, respectively, and then reacted at 4° C. for 16 hours to coat the plate. Thereafter, a blocking solution (5% Bovine serum albumin in TBS) was added to each well, reacted at room temperature for 1 hour, and then washed three times with TBS comprising 0.05% Tween 20. Then, AP-streptavidin conjugate (alkaline phosphatase-streptavidin conjugate) was diluted to 1:1,000 and then reacted at room temperature for 1 hour. After the reaction, the residual AP-streptavidin conjugate was removed again using TBS comprising 0.05% Tween 20. Then, a pNPP phosphatase substrate was added, and reacted for 20 minutes at room temperature. Then a stopping buffer was added to stop the reaction, and the absorbance was measured at a wavelength of 405 nm using VICTOR (available from PerkinElmer). As a result, as shown in FIG. 2, it was found that the 3× zinc oxide-binding peptide showed very high absorbance as compared with a single zinc oxide-binding peptide, and the absorbance was increased depending on the coated amount. The result shows that the quantitative analysis is possible using a binding strength of streptavidin and biotin of the zinc oxide-binding peptide.

Example 3

Figure 3:
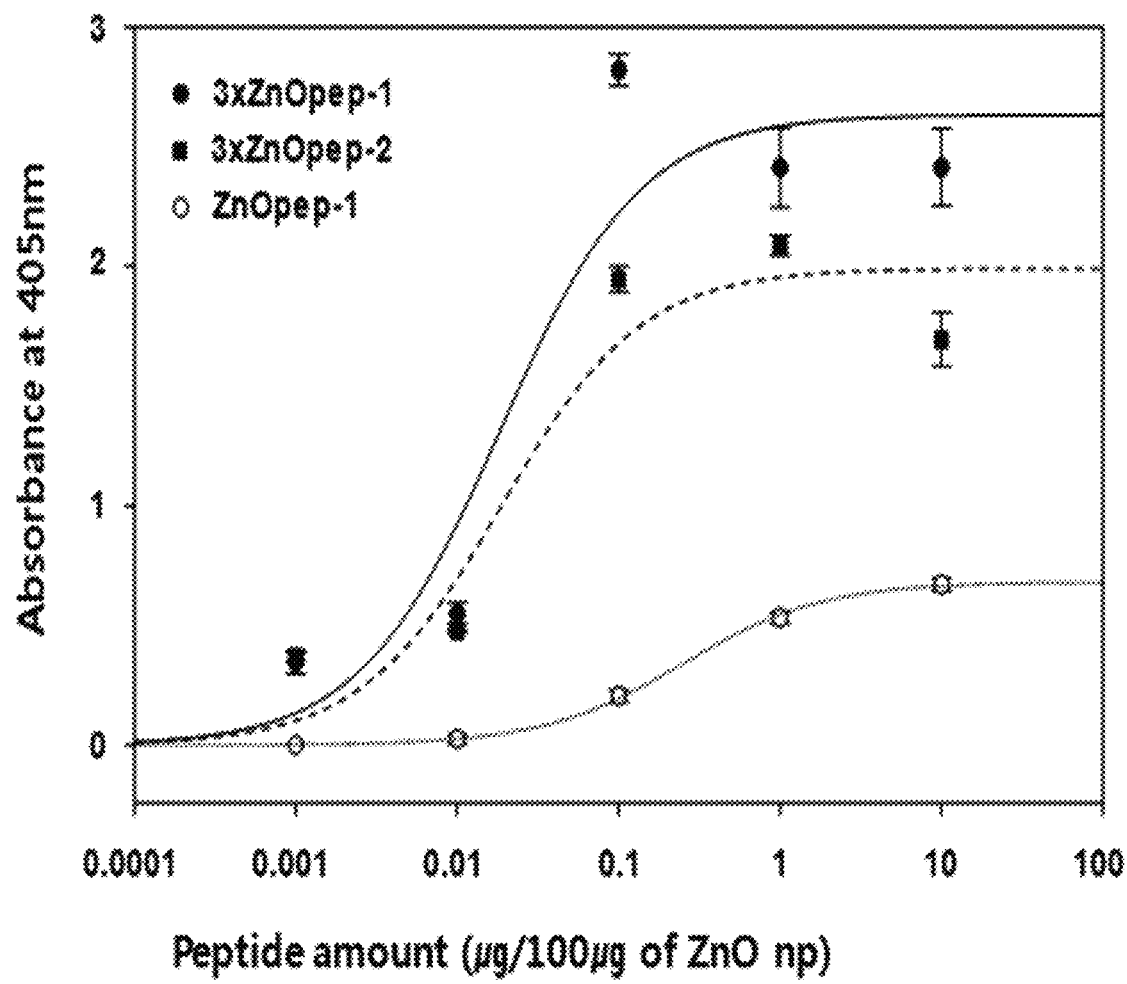
FIG. 3 shows the results of absorbance at 405 nm in which the amounts of ZnOpep-1, 3×ZnOpep-1, and 3×ZnOpep-2 of the present invention binding to the core-shell nanoparticles are measured.

Binding Strength Between Zinc Oxide Nanoparticles and Zinc Oxide-Binding Peptides In Example 3, a binding strength between the zinc oxide nanoparticles and zinc oxide-binding peptides based on Example 2 was confirmed. The zinc oxide nanoparticles (stored in ethanol) obtained from Example 1 were transferred to a 1.5 ml tube and then placed on a magnetic stand for 20 minutes to separate core-shell zinc oxide nanoparticles. The ethanol was completely removed from the zinc oxide nanoparticles, TBS was added, and then the nanoparticles were dispersed in an aqueous solution using ultrasonic waves. 100 μg of nanoparticles was mixed with 10 μg, 1 μg, 0.1 μg, 0.01 μg, and 0.001 μg of peptides, each of which was diluted with TBS, and then reacted at room temperature for 1 hour while stirring. After the reaction, a nanoparticle-peptide complexes were precipitated using a centrifuge (15,000 g, 2 min), and then placed on a magnetic stand for 15 minutes to separate the nanoparticle-peptide complexes. The complexes were washed six times with TBS using the same method. An AP-streptavidin conjugate (1.5 mg/ml) diluted to 1:1000 was added and then reacted for 1 hour while stirring. After reaction was finished, the AP-strepta-vidin conjugate was separated again using a centrifuge, placed for 15 minutes on a magnetic stand to remove a solution, and then washed six times with TBS. Thereafter, a pNPP phosphatase substrate was added and reacted at room temperature for 20 minutes, a stopping buffer was added to stop the reaction, and then an absorbance was measured at a wavelength of 405 nm using VICTOR (available from PerkinElmer). As a result, as shown in FIG. 3, it was found that the binding between the zinc oxide-binding peptides and the zinc oxide nanoparticles was increased depending on the concentration of the zinc oxide-binding peptides. In addition, it was found that the 3× zinc oxide-binding peptides bonded better with the zinc oxide nanoparticles as compared with the single zinc oxide-binding peptide. It was seen that each peptide bond was saturated when using about less than 1 µg of peptides (equivalent to approximately 1 nmol to 1×ZBP and approximately 0.3 nmol to 3×ZBP) based on 100 µg of core-shell nanoparticles so that about 3 to 10 pmol of peptide was bonded per 1 µg of core-shell nanoparticles.

Example 4

Figure 4:
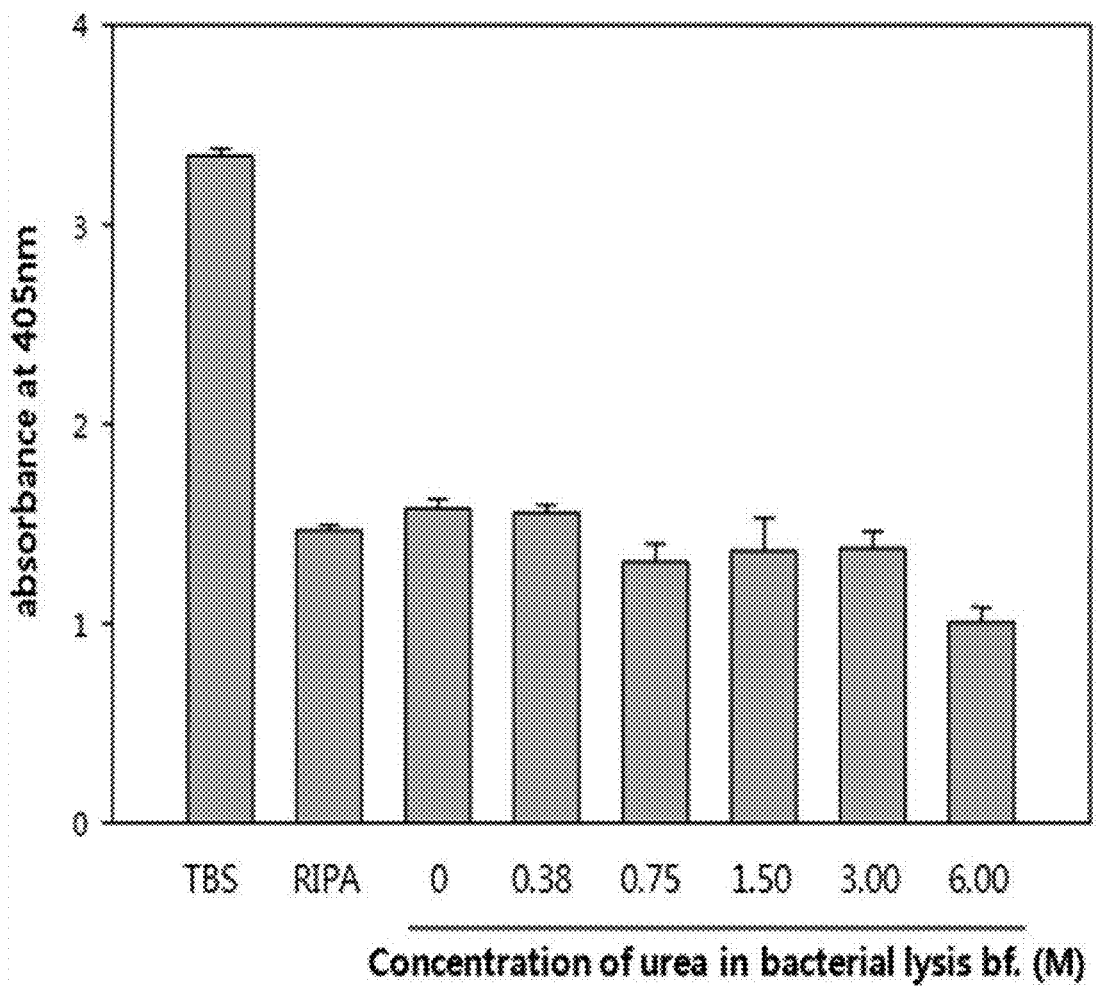
FIG. 4 shows the binding strength between the zinc oxide nanoparticles and the peptide in various kinds of aqueous solutions.

Binding Strength Between Zinc Oxide Nanoparticles and Zinc Oxide-Binding Peptides in Various Aqueous Solutions Example 4 was performed in order to confirm whether or not a binding strength between the zinc oxide nanoparticles and the zinc oxide-binding peptides as confirmed from Example 3 was possible in various aqueous solution conditions. The zinc oxide nanoparticles (stored in ethanol) obtained from Example 1 were transferred to a 1.5 ml tube, placed on a magnetic stand for 20 minutes to separate the core-shell zinc oxide particles, and then the ethanol was completely removed. The separated nanoparticles (100 µg) were floated in a bacterial lysis buffer (20 mM HEPES [pH 7.6], 500 mM NaCl, 1 mM EDTA, 1% NP-40) that was supplemented with TBS, an RIPA buffer (1% Triton X-100, 0.1% sodium dodecylsulfate, 0.5% sodium dioxycolate, 150 mM NaCl, 50 mM Tris-HCl [pH 7.5], 2 mM EDTA), or a urea with various concentrations (6 M, 3 M, 1.5 M, 0.75 M, 0.375 M), and 0.1 µg of peptide (3×ZnOpep-1) was added and then reacted while stirring at room temperature for 1 hour. The complexes were separated using a centrifuge and placed on a magnetic stand for 15 minutes, the aqueous solution was removed, and the complexes were then washed six times with TBS. An AP-streptavidin conjugate was added and reacted while stirring at room temperature for 1 hour. After the reaction was finished, the complexes were separated using a centrifuge and placed on a magnetic stand for 15 minutes, the reaction solution was removed, and the complexes were then washed six times with TBS. A pNPP phosphatase substrate was added and reacted at room temperature for 20 minutes, a reaction stopping buffer was added, and then an absorbance was measured at a wavelength of 405 nm. As a result, as shown in FIG. 4, it was found that the zinc oxide nanoparticles and the zinc oxide-binding peptides bonded well to each other even in the aqueous solution phase supplemented with TBS, RIPA, and the urea with various concentrations. This indicates that the zinc oxide nanoparticles and the zinc oxide-binding peptides bonded well even in various aqueous solution conditions.

Example 5

Preparation of Fusion Protein of Carcinoma Embryo Antigen and Zinc Oxide-Binding Peptides A human carcinoma embryo antigen (CEA) corresponding to amino acids 35 to 332 (GenBank Accession no. M17303) was purified from *E. coli* using a method as disclosed in Bae, M. Y., et al. [Bae, M. Y., Cho, N. H. & Seong, S. Y. Protective anti-tumor immune responses by murine dendritic cells pulsed with recombinant Tat-carcinoembryonic antigen derived from *Escherichia coli. Clin. Exper. Immunol.* 157, 128-138 (2009)]. In order to prepare a recombinant ZBP-CEA fusion protein, annealed double-stranded DNA (5'-<u>CTAGCC</u> GCC CGC ATC GCA AAG GCG GCG ATG CGC GCC CGC ATC GCA AAG GCG GCG ATG CGC GCC CGC ATC GCA AAG GCG GCG ATG CG<u>G</u>-3') coding for 3×ZnOpep-1 (RPHRKGGDAR-PHRKGGDARPHRKGGDA) was cleaved at NheI and EcoRI sites (underlined parts) and then cloned to a pET23a-CEA plasmid as disclosed in Bae, M. Y., et al. as mentioned above. The recombinant protein was produced and purified according to the method as disclosed in Bae, M. Y., et al. ZnOpep-1, ZnOpep-2, and 3×ZnOpep-2 were produced according to the same method. The purified protein was treated with an endotoxin-removed column (Pierce) before its use. The endotoxin contamination of the purified recombinant protein was investigated using QCI-1000 End-Point Chromagenic Endotoxin detection kit (Lonza).

Example 6

Figure 5:
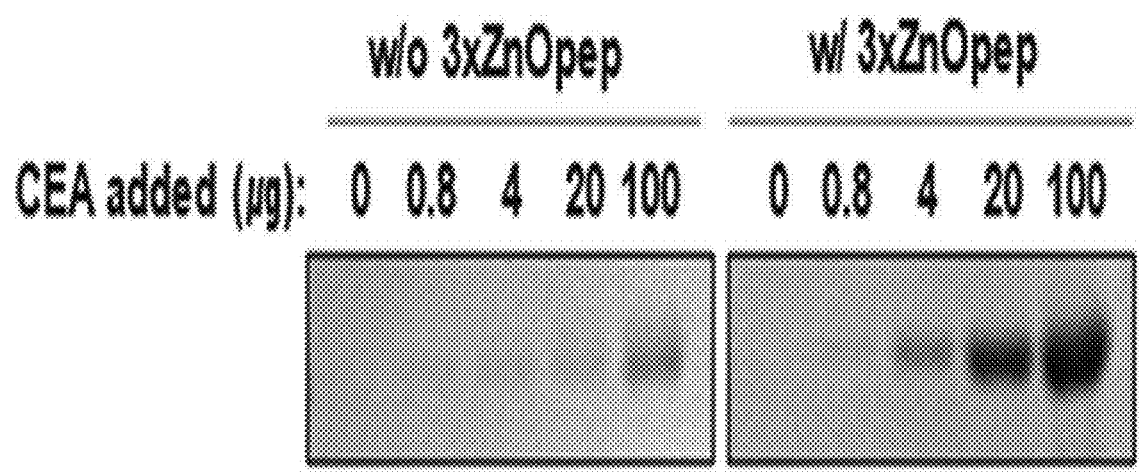
FIG. 5 shows the binding strength between the zinc oxide nanoparticles and the recombinant protein of a CEA tumor antigen comprising the zinc oxide-binding peptides in an aqueous solution.

Binding Strength of Recombinant CEA Tumor Antigen Comprising Zinc Oxide-Binding Peptides Amino Acid Sequences and Zinc Oxide Nanoparticles Example 5 was performed to confirm a binding strength of the recombinant carcino-embryonic antigen (CEA) comprising amino acid sequences of the zinc oxide-binding peptides and the zinc oxide nanoparticles. The recombinant CEA tumor antigen comprising the zinc oxide-binding peptide with different concentrations and the tumor antigen without the zinc oxide-binding peptides were reacted with 50 µg of zinc oxide nanoparticles and phosphate-buffered saline (PBS) for 1 hour. After reaction was finished, the complexes were separated again using a centrifuge and placed on a magnetic stand for 15 minutes, the solution was removed, and the complexes were then washed six times with PBS. The collected zinc oxide nanoparticles were added to an SDS-PAGE sample buffer, reacted at 100° C. for 10 minutes, subjected to SDS-PAGE, and then the amount of the recombinant protein bonded to the zinc oxide nanoparticles was confirmed using Coomassie blue staining. As a result, as shown in FIG. 5, it was found that a very small amount of the recombinant CEA tumor antigen without the amino acid sequences of the zinc oxide-binding peptides was bonded to the zinc oxide nanoparticles, while the amount of the recombinant CEA tumor antigen comprising the amino acid sequences of the zinc oxide-binding peptides that was bonded to the zinc oxide nanoparticles was increased depending on the concentration of peptides added. This indicates that the binding between the zinc oxide nanoparticles and the recombinant tumor antigen comprising the amino acid sequences of the zinc oxide-binding peptides is possible.

Example 7

Figure 6:
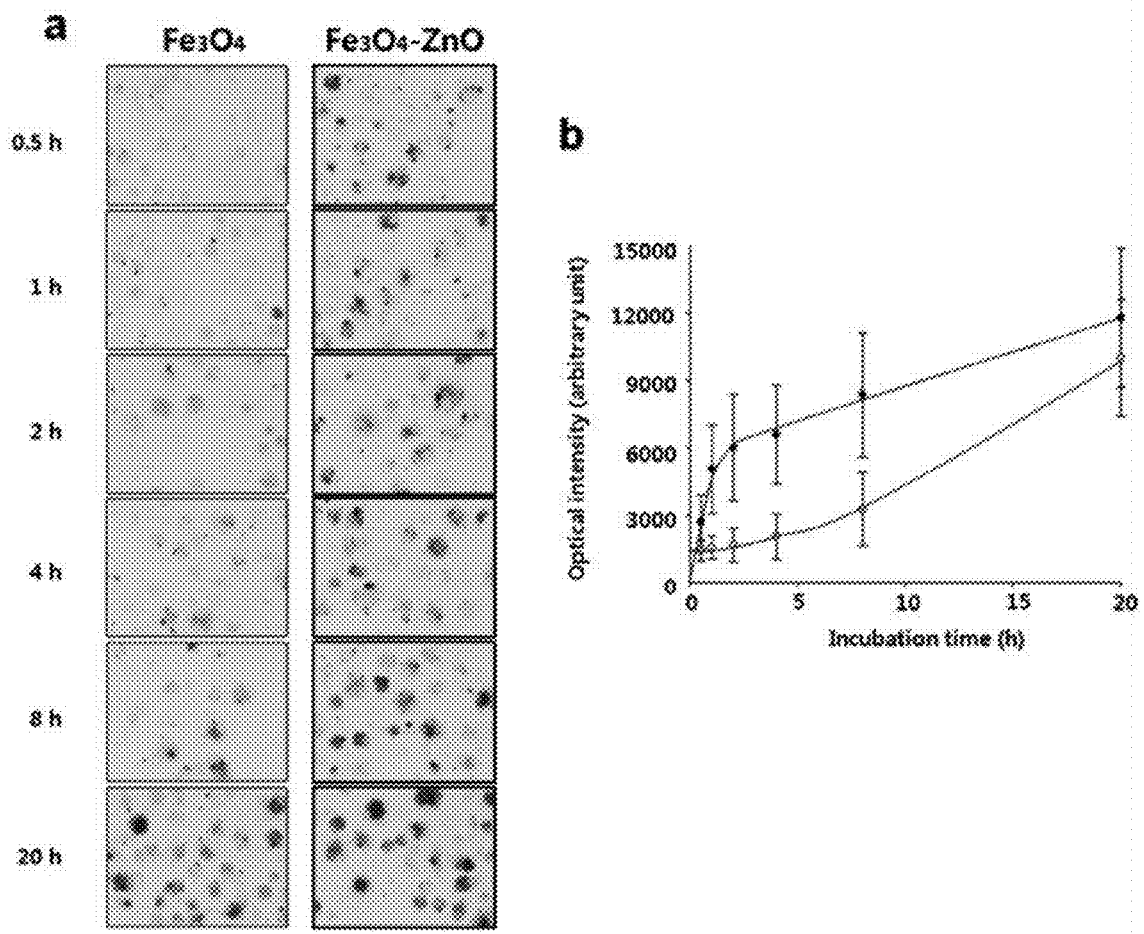
FIG. 6A shows the delivery of $Fe_3O_4$ nanoparticles and $Fe_3O_4$—ZnO core-shell nanoparticles in a cell according to an incubation time through DAB-enhanced Prussian blue staining.
FIG. 6B shows the results of measuring the optical strength of 100 cells randomly selected from each sample.

In Vitro Monitoring of CEA Tumor Antigen Complex Comprising Zinc Oxide Nanoparticles and Amino Acid Sequences of Zinc Oxide-Binding Peptides Loaded on Dendritic Cells Dendritic cells were prepared from a mouse cell using the method as disclosed in Bae, M. Y., et al., and then the core-shell nanoparticles were loaded on the dendritic cell. Immature dendritic cells were co-cultured with the core-shell nanoparticles. This is because the phagocytosis of the immature dendritic cells was active as compared with the mature dendritic cells. In order to determine the effect the an incubation time and the loading efficiency of a ZnO shell, the immature dendritic cells were incubated with 100 µg/ml of $Fe_3O_4$ NPs or $Fe_3O_4$—ZnO core-shell nanoparticles under various time conditions. The introduced nanoparticles were detected by DAB (diaminobenzidine)-enhanced Prussian blue staining and a quantitative analysis was performed by measuring an optical intensity. FIG. 6A shows the delivery of $Fe_3O_4$ NPs and $Fe_3O_4$—ZnO core-shell nanoparticles in a cell according to the incubation time through DAB-enhanced Prussian blue staining, and FIG. 6B shows the results of measuring an optical intensity of 100 cells randomly selected from each sample. As shown in FIG. 6, $Fe_3O_4$—ZnO core-shell nanoparticles were more effectively ingested by the dendritic cells as compared with $Fe_3O_4$ NPs in a reaction time of 8 hours or less, but there were no differences after an incubation time of 20 hours. As a result, it was found that the ZnO shell promotes the delivery of the core-shell nanoparticles in a cell, and when using the core-shell nanoparticles, the incubation time required for introduction into the dendritic cells can be decreased.

Figure 7:
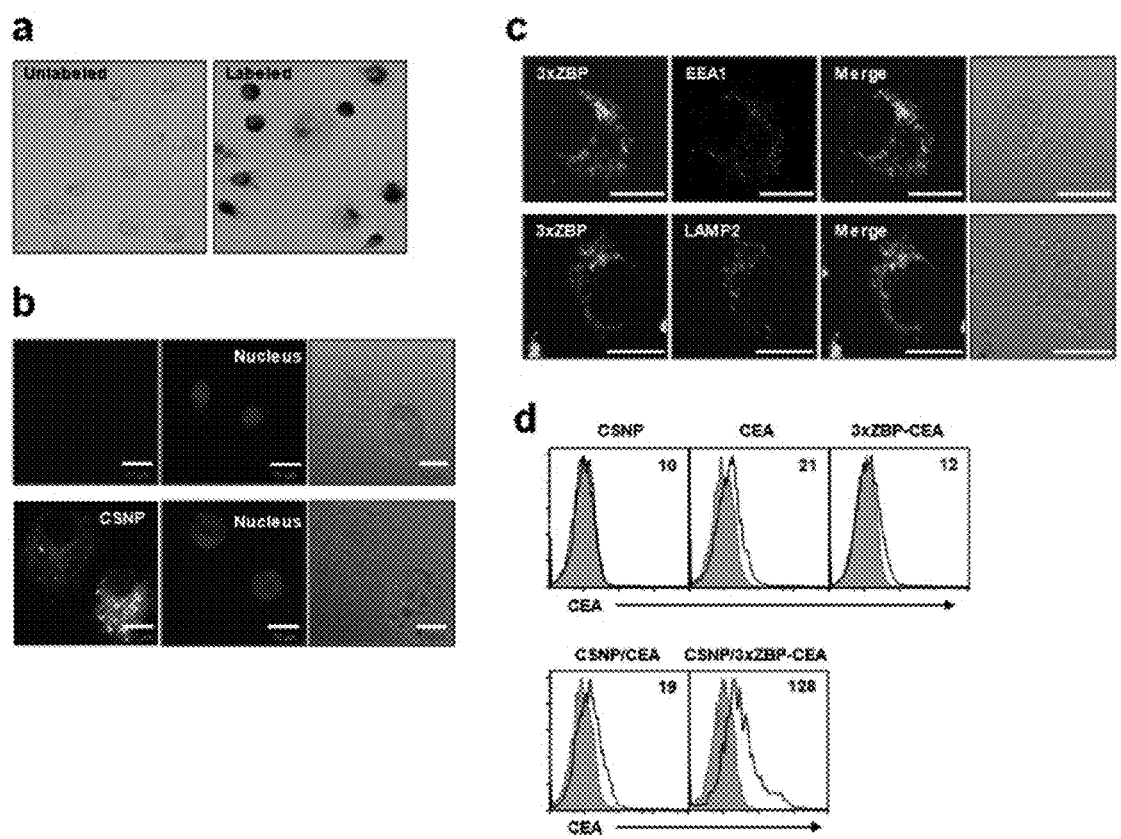
FIG. 7A shows the observation results of the core-shell nanoparticles introduced into the dendritic cells through DAB-enhanced Prussian blue staining.
FIG. 7B shows the observation results of the introduced core-shell nanoparticles with a confocal fluorescence microscope using an optical property of the core-shell nanoparticles.
FIG. 7C shows the observation results of the peptides binding with the core-shell nanoparticles introduced into the dendritic cells with a confocal fluorescence scanning microscope.
FIG. 7D shows the FACS analysis results of the amount of tumor antigen present on the dendritic cells when the recombinant protein of the CEA tumor antigen comprising the zinc oxide-binding peptides and the zinc oxide nanoparticles and the zinc oxide nanoparticles are delivered in the dendritic cell.

FIG. 7 shows the results of in vitro monitoring of an antigen loaded on the dendritic cells using an optical property of the core-shell nanoparticles. FIG. 7A shows the dendritic cells not loaded with the core-shell nanoparticles and the dendritic cells loaded with the visible core-shell nanoparticles after DAB-enhanced Prussian blue staining. As shown in FIG. 7A, about at least 95% of the dendritic cells were labeled with the core-shell nanoparticles after an incubation time of 1 hour. It is well known that ZnO nanoparticles are effectively ingested by a phagocytic cell and a non-phagocytic cell within hours. A precise mechanism was not confirmed, but the results suggest that the surface coating of $Fe_3O_4$ NPs by ZnO may promote cellular uptake. Considering that the general superparamagnetic $Fe_3O_4$ particles may require a transfection-promoting compound, such as protamine sulfate or a long incubation time (about 16 to 48 hours) for delivery in a cell, the core-shell nanoparticles of the present invention have great advantages in that a short time for incubation is required, and a reagent for transfection and surface modification are not required.

Photoluminescence of ZnO was investigated using a laser scanning confocal microscope after the delivery in a dendritic cell cytosol. FIG. 7B shows the observation results of the dendritic cells (lower end) loaded with the core-cell nanoparticles or the dendritic cells (upper end) not loaded with the core-shell nanoparticles using a confocal microscope (excitation: 405 nm, eradiation: >420 nm). The nucleus of the dendritic cells stained with ToPro-3 staining reagent exhibited a blue color (white bar: 10 μm). The core-shell nanoparticle-labeled dendritic cells was excited at a wavelength of 405 nm, and showed high fluorescence intensity at a wide emitting wavelength of 465 to 679 nm. However, a peak emission was observed at 529 to 550 nm, and could be easily observed through a confocal microscope or a general FACS (not shown). The core-shell nanoparticles were dispersed through a cytoplasm, and observed in a cohesion type, which indicates that the core-shell nanoparticles were ingested by phagocytosis. HeLa cell derived from non-phagocytotic epithelium had a similar pattern to the core shell nanoparticle distribution (data not shown). Co-staining of endosome or lysosome vesicles shows that the cohesive core-shell nanoparticles and EEA1 (an initial endosome marker) or LAMP2 (a lysosome marker) co-exist, which indicates that the cohesive nanoparticles are internalized through endocytosis. Considering that the core-shell nanoparticles were detected in cytoplasm and intracellular trafficking vesicles, the core-shell nanoparticles were regarded as being internalized by the phagocytosis or endocytosis.

Intracellular delivery of polypeptides fixed on the core-shell nanoparticles was also investigated. As shown in FIG. 7C, the 3×ZBP-bonded core-shell nanoparticles were effectively delivered in the cytoplasm of the dendritic cells. Some peptide-core shell nanoparticle aggregates partially co-existed in the endosome or lysosome with the core-shell nanoparticles without peptides (white bar: 10 μm).

Example 8

Delivery Efficiency of CEA Tumor Antigen Complex Comprising Zinc Oxide Nanoparticles and Amino Acid Sequences of Zinc Oxide-Binding Peptides Example 8 was performed to confirm the efficiency of delivery of CEA tumor antigen complexes comprising the zinc oxide nanoparticles and the amino acid sequences of the zinc oxide-binding peptides into the dendritic cells. The efficiency of delivery of the CEA tumor antigen complexes comprising the zinc oxide nanoparticles and the amino acid sequences of the zinc oxide-binding peptides in the dendritic cells was confirmed using FACS analysis. Immature dendritic cells ($1 \times 10^6$ cells) isolated from bone marrow of a mouse were reacted with a CEA tumor antigen at 37° C. for 1 hour, and then the amount of tumor antigen delivered into a cell was analyzed with FACS. The complexes of zinc oxide nanoparticles (50 μg) and the CEA tumor antigen (20 μg) were reacted in PBS for 1 hour.

As a control group and an experimental group, the CEA tumor antigen was divided into a) a group treated with the zinc oxide nanoparticles, b) a group treated with the CEA tumor antigen, c) a group treated with the recombinant CEA tumor antigen comprising the zinc oxide-binding peptide, d) a group co-treated with the zinc oxide nanoparticles and the CEA tumor antigen, and e) a group treated with the CEA tumor antigen complexes comprising the zinc oxide nanoparticles and the amino acid sequences of the zinc oxide-binding peptides, and then analyzed. As a result, as shown in FIG. 7D, it was found that the CEA tumor antigen was delivered into the dendritic cells only for the experimental group that can form the CEA tumor antigen complexes comprising the zinc oxide nanoparticles and the amino acid sequences of the zinc oxide-binding peptides (core-shell nanoparticles: zinc oxide core-shell nanoparticles, CEA: tumor antigen, 3Xzbp-CEA: tumor antigen bonded with zinc oxide-binding peptides (3×ZnOpep-1)). This indicates that the zinc oxide nanoparticles can be used as a carrier that can introduce CEA tumor antigen complexes comprising the zinc oxide-binding peptides into the dendritic cells.

Example 9

Figure 8:
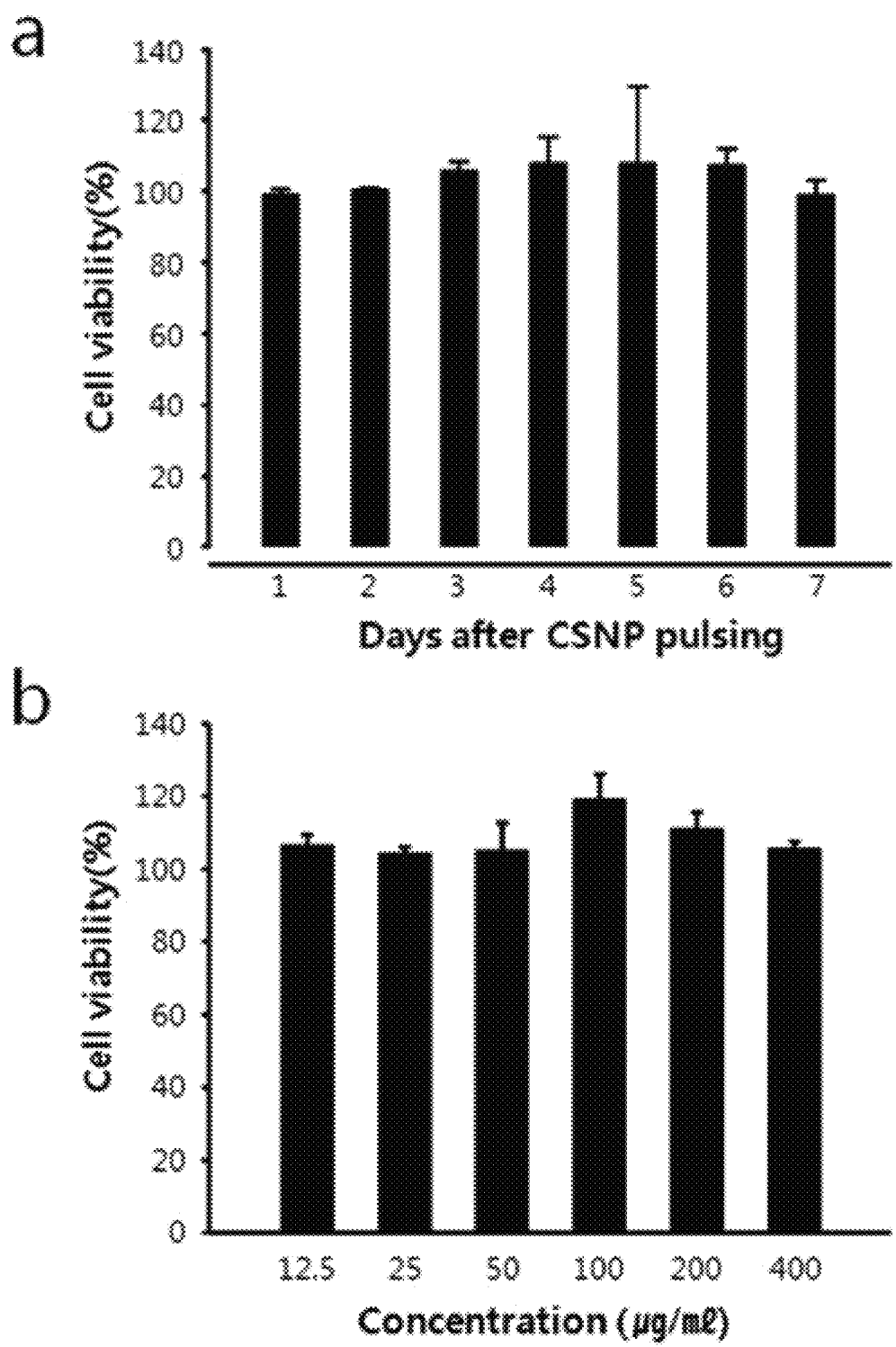
FIG. 8 is a graph showing that the loading of the core-shell nanoparticles does not affect cell viability of the dendritic cell.
Figure 9:
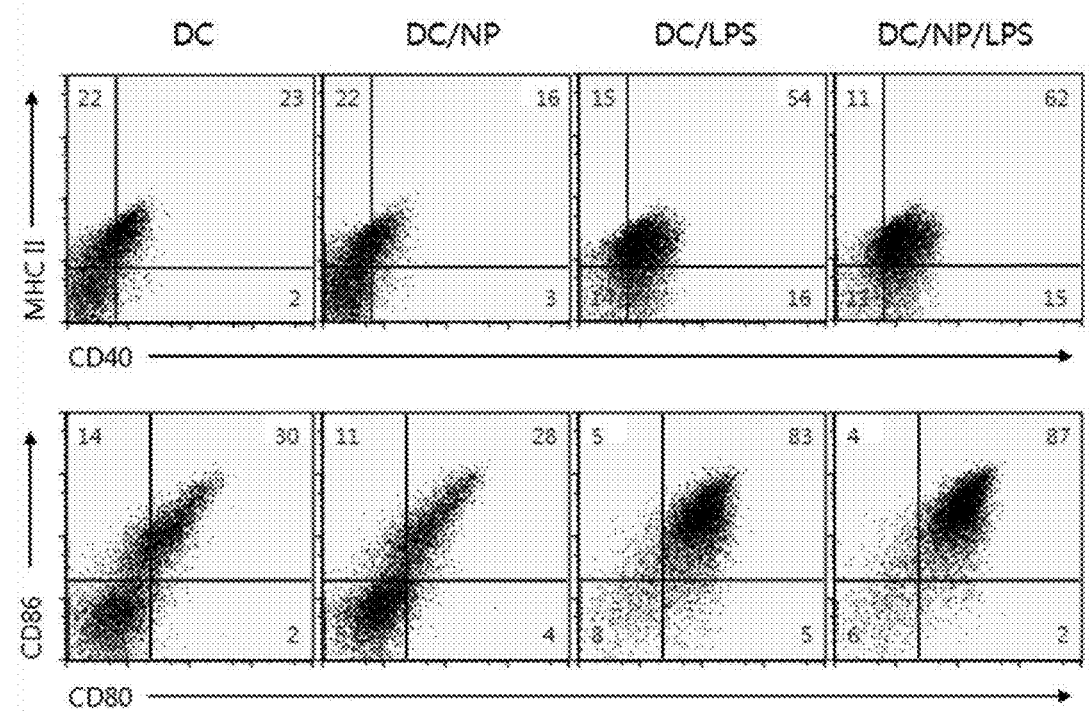
FIG. 9 is a graph showing that the loading of the core-shell nanoparticles does not affect maturation of the dendritic cell.

Viability and Maturation of Dendritic Cells According to Delivery of CEA Tumor Antigen Complex Comprising Zinc Oxide Nanoparticles and Amino Acid Sequences of Zinc Oxide-Binding Peptides into Dendritic Cells The effects of loading of the core-shell nanoparticles on viability and maturation of the dendritic cells were estimated. FIG. 8A shows cell viability when 100 μg/ml of the core-shell nanoparticles were incubated with the dendritic cells for 1 to 7 days, and FIG. 8B shows cell viability when the core-shell nanoparticles with various concentrations (12.5 to 400 μg/ml) were incubated with the dendritic cells for three days. As shown in FIG. 8, the loading of the core-shell nanoparticles does not affect the cell viability of the dendritic cells. FIG. 9 shows a mature marker of the dendritic cells before and after loading of the core-shell nanoparticles. Lipopolysaccharide (LPS) of bacteria was used to mature the dendritic cells. Surface expression of the mature marker (MHC II, CD40, CD80, and CD86) on the dendritic cells was not affected by the loading of the core-shell nanoparticles. In conclusion, the results suggest that the loading of the core-shell nanoparticles does not affect cell viability or maturation of the dendritic cells.

Example 10

Figure 10:
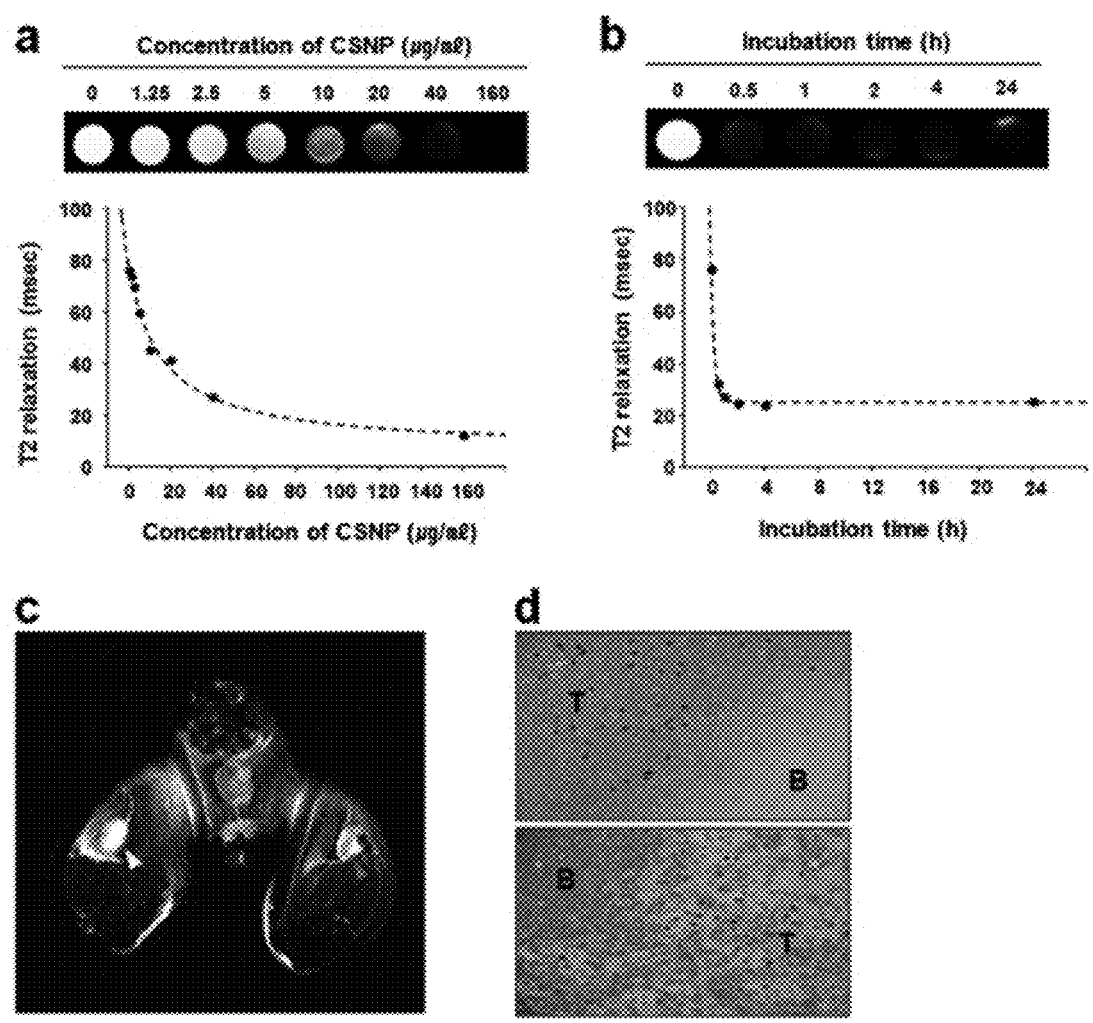
FIG. 10 shows in vivo and in vitro detection results by an MRI analysis of the dendritic cells labeled with the core-shell nanoparticles and the iron oxide nanoparticles.
Figure 11:
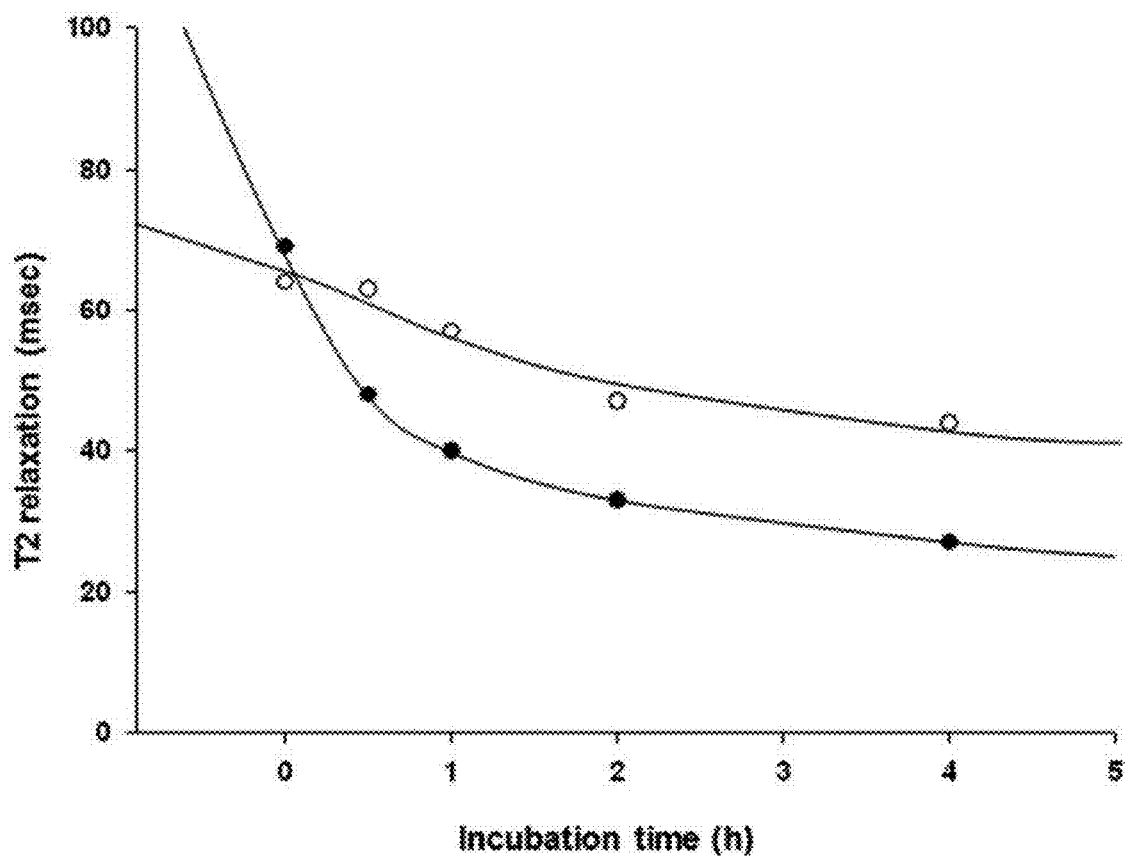
FIG. 11 shows the results of the MRI analysis comparing T2 relaxation time of the dendritic cells (●) labeled with the core-shell nanoparticles and the dendritic cell (○) labeled with the iron oxide nanoparticles.

Detection In Vivo and In Vitro by MRI Analysis of Dendritic Cell Labeled with CEA Tumor Antigen Complex Comprising Zinc Oxide Nanoparticles and Amino Acid Sequences of Zinc Oxide-Binding Peptides For in vivo or in vitro MRI experiments using the nanoparticles, it is very important to determine an optimum condition for effective cell labeling. To achieve this, the dendritic cells were first incubated with the core-shell nanoparticles with various concentrations (0 through 160 µg/ml). As shown in FIG. 10A, the results of in vitro MRI imaging of the dendritic cells shows that the T2 relaxation time was gradually decreased according to the increase in concentration of the core-shell nanoparticles (image darkens), and the dendritic cells were saturated at less than 100 µg/ml. In order to determine the optimal incubation time, the dendritic cells were cultured for 0.5 to 24 hours in the presence of 40 µg/ml of core-shell nanoparticles. As shown in FIG. 10B, the dendritic cells were saturated with the core-shell nanoparticles within 1 hour, and as mentioned above, this indicates that the core-shell nanoparticles were effectively ingested by the dendritic cell within 1 hour, and T2 relaxation time was sufficiently decreased for the MRI. As shown in FIG. 11, the MRI analysis results of the core-shell nanoparticle-labeled dendritic cells (●) show that T2 relaxation time was more quickly decreased for the first 4 hours as compared with the $Fe_3O_4$-labeled dendritic cells (○). The results show that the core-shell nanoparticles can be applied to monitor the delivery of the dendritic cells in vivo using non-invasive MRI analysis.

In order to verify the potential use of the core-shell nanoparticles for in vitro monitoring of the delivery of the dendritic cells by the MRI analysis, the dendritic cells labeled with the core-shell nanoparticles were injected to the back sole of a C57BL/6 mouse's foot. The dendritic cells transferred to a popliteal lymph node from the injected back sole were observed using T2-weighted multigradient echo magnetic resonance sequence. As shown in FIG. 10C, an area showing hypointense that exhibited the presence of the core-shell nanoparticle-labeled cell in the left lymph node was observed 48 hours after injection (red arrow). As expected, the decrease of T2 was not observed in the popliteal lymph node corresponding to the injection part of ZnO NP-labeled dendritic cells (white arrow).

The core-shell nanoparticle-labeled dendritic cells were observed at a central part of the draining lymph node, which indicates that the decrease of T2 was due to the core-shell nanoparticle-labeled dendritic cells rather than the core-shell nanoparticles delivered through a lymphatic vessel. Free nanoparticles were delivered through a lymphatic vessel and then located at the subcapsular region of the lymph node. An immunohistology assay of the cut lymph node shows that the decrease of T2 by MRI analysis was caused by the core-shell nanoparticle-labeled dendritic cells transferred to the T cell area (FIG. 10D). When combining the results of DAB-enhanced Prussian blue staining and immunohistochemistry (anti-Thy1.2, the upper panel of FIG. 10D; anti-B220, the lower panel of FIG. 10D), it was found that most of the core-shell nanoparticle-labeled dendritic cells were present in the Thy1.2+ T cell area, not in the B220+ B cell follicle. In contrast, an iron component was not observed in the lymph node injected with the zinc oxide-labeled DCs.

Example 11

Figure 12:
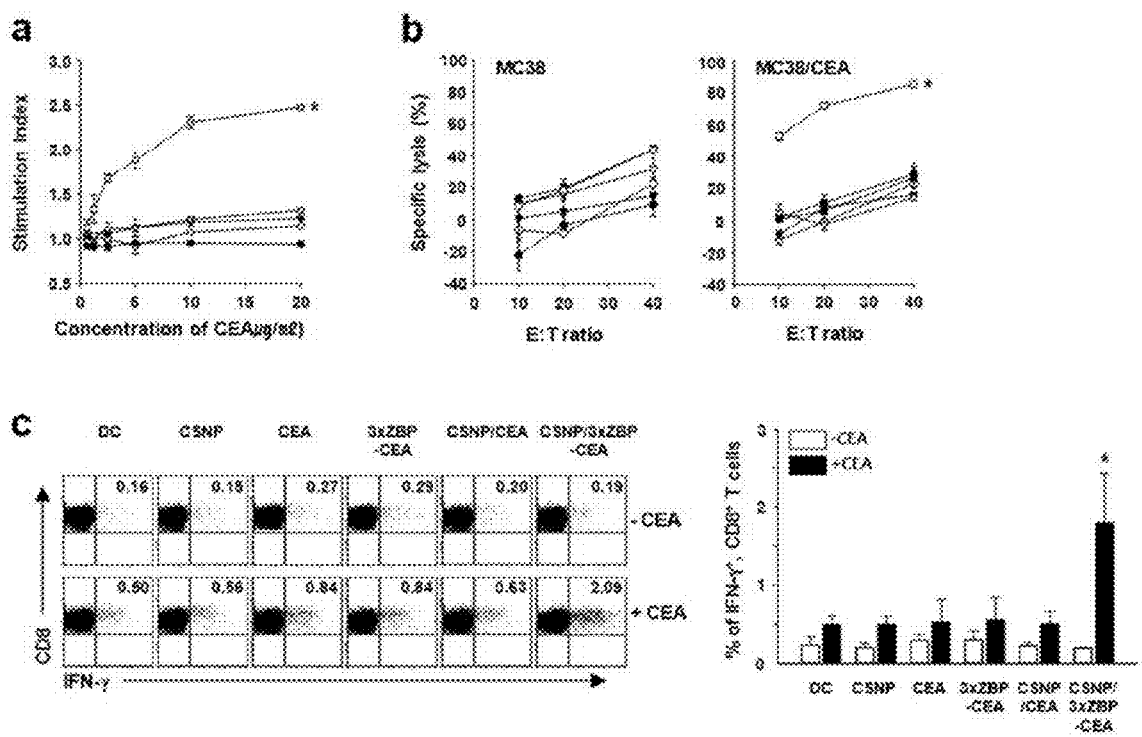
FIG. 12 shows an assessment result of anti-tumor immunity induced with the dendritic cells labeled with the CEA tumor antigen complex comprising the zinc oxide nanoparticles and the amino acid sequences coding for the zinc oxide-binding peptides.
Figure 13:
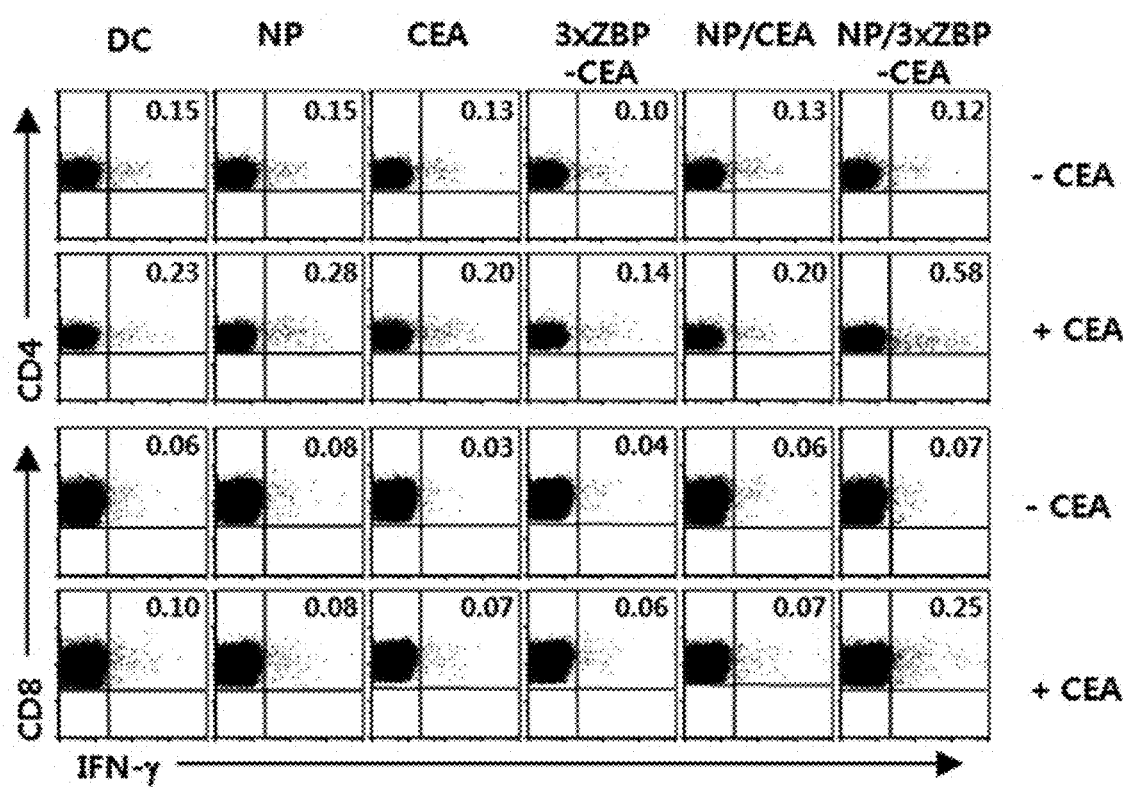
FIG. 13 shows an inducement result of the CEA-specific T cell response induced by the dendritic cells labeled with the CEA tumor antigen complex comprising the zinc oxide nanoparticles and the amino acid sequences coding for the zinc oxide-binding peptides.

Anti-Tumor Immunity Induced with Dendritic Cells Labeled with CEA Tumor Antigen Complex Comprising Zinc Oxide Nanoparticles and Amino Acid Sequences of Zinc Oxide-Binding Peptides C57BL/6 mice were immunized with the dendritic cells labeled with the CEA tumor antigen complex comprising the zinc oxide nanoparticles and the amino acid sequences of the zinc oxide-binding peptides, and then CEA-specific cellular immunity was analyzed. A lymphocyte was obtained from the spleen of the immunized mice, and CEA with various concentrations was re-stimulated in vitro. As shown in FIG. 12A, the lymphocyte of the mouse immunized with the dendritic cells (core-shell nanoparticles/3×ZBPCEA) showed very high dosage-dependent proliferation for the reaction to CEA as compared with the lymphocyte of the control. Splenocyte obtained from the immunized mouse was analyzed in order to investigate whether or not the CEA-specific cellulotoxic lymphocyte was generated systemically. When using the splenocyte from the mouse immunized with the dendritic cells (core-shell nanoparticles/3×ZBP-CEA), a significant cytotoxic reaction was observed to CEA-expressing tumor cell (MC38/CEA), but no significant cytotoxicity was observed in the control (the right panel of FIG. 12B). The cytotoxicity of splenocyte to a CEA-negative MC38 target cell was not significantly exhibited in any of the experimental groups (the left panel of FIG. 12B). This suggests that the reaction detected in the immunized mouse was specific to tumor antigen CEA. Next, T cell generation was investigated, in which T cell generates IFN-γ that is a typical labeling cytokine of a cell-mediated immune response. In the splenocyte, a CEA-specific CD8+ T cell immune response was investigated through cellular cytokine staining, and a flowcytometry in the presence or absence of a CEA antigen. The frequency of IFN-γ-secretory CD8+ T cell was increased by about ten times after stimulation with only the tumor antigen in only the CD8+ T cell obtained from the mouse immunized with the dendritic cells (core-shell nanoparticles/3×ZBP-CEA). In contrast, the CD8+ T cell obtained from the other control did not exhibit a significant IFN-γ secretion after immunization (FIG. 12C). The dendritic cell (core-shell nanoparticles/3×ZBPCEA)-treated group was more effective on generation of the CEA-specific IFN-γ-generating CD4+ or CD8+ T cells in the lymphocyte as compared with the other dendritic cell-treated group (FIG. 13). The results show that the dendritic cells (core-shell nanoparticles/3×ZBP-CEA) can effectively generate the CEA-specific cellular immunity in vivo.

Figure 14:
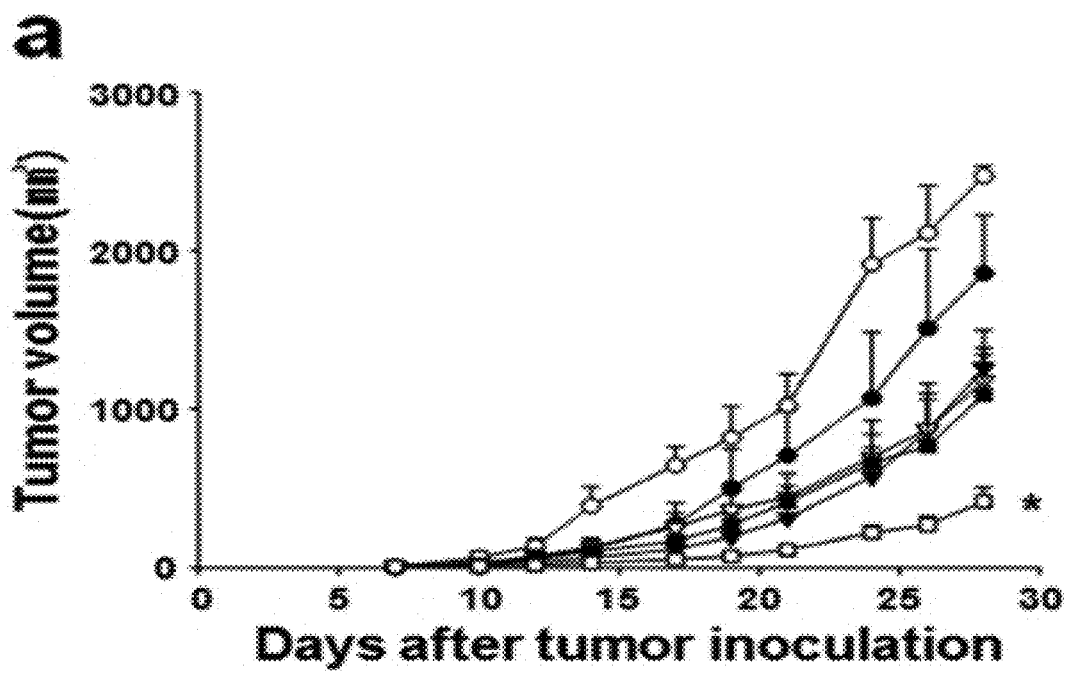
FIG. 14 shows an analysis result of tumor growth and viability of a mouse immunized with the dendritic cells labeled with the CEA tumor antigen complex comprising the zinc oxide nanoparticles and the amino acid sequences coding for the zinc oxide-binding peptides (□: NP/3×ZBP-CEA, ■: NP/CEA, : 3×ZBP-CEA, ▼: CEA, ○: NP, ●: DC).
Figure 14:
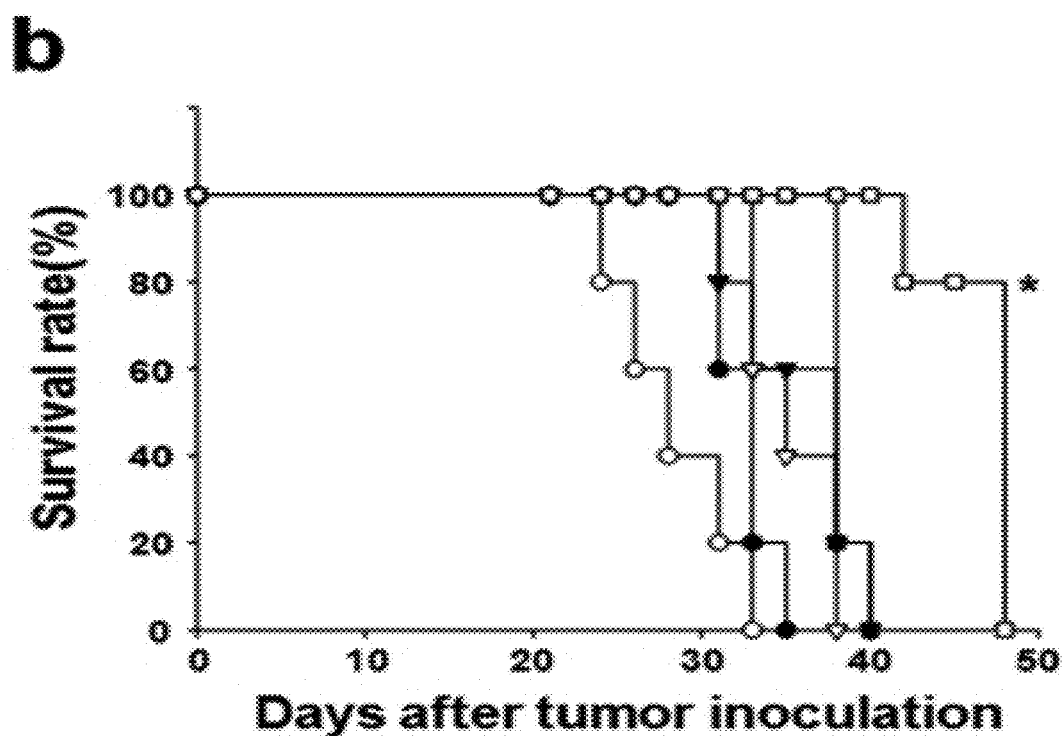

An MC38/CEA cell was injected into the side of C57BL/6 mice. The anti-tumor immunity of the dendritic cells (core-shell nanoparticles/3×ZBP-CEA) was evaluated by observing the growth of a tumor according to the dendritic cell (core-shell nanoparticles/3×ZBP-CEA) immunization. Seven days after the tumor injection, the mice were immunized four times with the dendritic cells once a week. As shown in FIG. 14A, the growth of the tumor was more suppressed in the mouse injected with the dendritic cells (core-shell nanoparticles/3×ZBP-CEA) as compared with the control (□: NP/3×ZBP-CEA, ■: NP/CEA, : 3×ZBP-CEA, ▼: CEA, ○: NP, ●: DC). In addition, as shown in FIG. 14B, 40 days after the tumor injection, all five mice treated with the dendritic cells (core-shell nanoparticles/3× ZBP-CEA) had survived, whereas mice of all other groups had died. An average survival time of the mice immunized with the dendritic cells (core-shell nanoparticles/3×ZBP-CEA) was extended an average of 10.5 to 19.5 days as compared with the control mice. The results show that the dendritic cells (core-shell nanoparticles/3×ZBP-CEA) induce a stronger and more powerful immune response to the CEA-positive tumor as compared with the control.

What is claimed is:

1. A vaccine composition comprising a complex of a zinc oxide nanoparticle and a recombinant protein, wherein the recombinant protein comprises a zinc oxide-binding peptide and an antigen, and an immunocyte, wherein the complex is introduced into the immunocyte.

2. The vaccine composition of claim 1, wherein the specific zinc oxide-binding peptide has the structure of the following Formula I or Formula II:

$$[(Arg-X_1-X_2-Arg)_m-linker]_n \quad [Formula\ 1]$$

$$[(Arg-X_1-X_2-Arg-Lys)_m-linker]_n \quad [Formula\ 2]$$

SEQUENCE LISTING

```
<160> NUMBER OF SEQ ID NOS: 4

<210> SEQ ID NO 1
<211> LENGTH: 9
<212> TYPE: PRT
<213> ORGANISM: Artificial
<220> FEATURE:
<223> OTHER INFORMATION: synthetic peptide

<400> SEQUENCE: 1

Arg Pro His Arg Lys Gly Gly Asp Ala
1               5

<210> SEQ ID NO 2
<211> LENGTH: 9
<212> TYPE: PRT
<213> ORGANISM: Artificial
<220> FEATURE:
<223> OTHER INFORMATION: synthetic peptide

<400> SEQUENCE: 2

Arg Thr His Arg Lys Gly Gly Asp Ala
1               5

<210> SEQ ID NO 3
<211> LENGTH: 27
<212> TYPE: PRT
<213> ORGANISM: Artificial
<220> FEATURE:
<223> OTHER INFORMATION: synthetic peptide

<400> SEQUENCE: 3

Arg Pro His Arg Lys Gly Gly Asp Ala Arg Pro His Arg Lys Gly Gly
1               5                   10                  15

Asp Ala Arg Pro His Arg Lys Gly Gly Asp Ala
            20                  25

<210> SEQ ID NO 4
<211> LENGTH: 27
<212> TYPE: PRT
<213> ORGANISM: Artificial
<220> FEATURE:
<223> OTHER INFORMATION: synthetic peptide

<400> SEQUENCE: 4

Arg Thr His Arg Lys Gly Gly Asp Ala Arg Thr His Arg Lys Gly Gly
1               5                   10                  15

Asp Ala Arg Thr His Arg Lys Gly Gly Asp Ala
            20                  25
``` wherein,
$X_1$ is Pro, Ala, Thr, Gln, or Be;
$X_2$ is His, Be, Asn, or Arg;
m is an integer of 1 to 5; and
n is an integer of 1 to 100.

3. The vaccine composition of claim 1, wherein the antigen is a tumor antigen.

4. The vaccine composition of claim 3, wherein the tumor antigen is selected from the group consisting of a carcinoma embryonic antigen, survivin, MAGE-1, MAGE-2, MAGE-3, MAGE-12, BAGE, GAGE, NY-ESO-1, tyrosinase, TRP-1, TRP-2, gp100, MART-1, MC1R, Ig idiotype, CDK4, caspase-9, beta-catenin, CIA, BCR/ABL, mutated p21/ras, mutated p53, proteinase 3, WT1, MUC-1, normal p53, Her2/neu, PAP, PSA, PSMA, G250, HPV E6/E7, EBV LMP2a, HCV, HHV-8, alpha-fetoprotein, 5T4, onco-trophoblast, and glycoprotein.

5. The vaccine composition of claim 1, wherein the immunocyte is a dendritic cell, T cell, or NK cell.

6. The vaccine composition of claim 1, wherein the zinc oxide nanoparticle has a core-shell structure, and wherein the core is composed of a T1 or T2 contrast medium and the shell is composed of zinc oxide.

* * * * *